United States Patent
Jass et al.

(10) Patent No.: US 8,614,346 B2
(45) Date of Patent: Dec. 24, 2013

(54) METHODS AND COMPOSITIONS FOR PREPARATION OF AMPHETAMINE CONJUGATES AND SALTS THEREOF

(75) Inventors: Paul Alan Jass, Peculiar, MO (US); Todd Jeffrey Johnson, Olds, IA (US); Jason Scott Douglas, Charles City, IA (US); Matthew Wendell Schiesher, Charles City, IA (US)

(73) Assignee: Cambrex Charles City, Inc., Charles City, IA (US)

( * ) Notice: Subject to any disclaimer, the term of this patent is extended or adjusted under 35 U.S.C. 154(b) by 128 days.

(21) Appl. No.: 13/378,176

(22) PCT Filed: Jun. 18, 2010

(86) PCT No.: PCT/US2010/039174
§ 371 (c)(1),
(2), (4) Date: Feb. 15, 2012

(87) PCT Pub. No.: WO2010/148305
PCT Pub. Date: Dec. 23, 2010

(65) Prior Publication Data
US 2012/0190880 A1    Jul. 26, 2012

Related U.S. Application Data

(60) Provisional application No. 61/218,719, filed on Jun. 19, 2009.

(51) Int. Cl.
| | | |
|---|---|---|
| C07C 231/12 | (2006.01) | |
| C07C 271/20 | (2006.01) | |
| C07C 303/32 | (2006.01) | |
| C07C 237/22 | (2006.01) | |

(52) U.S. Cl.
USPC .............. 560/25; 562/114; 564/153; 564/196

(58) Field of Classification Search
None
See application file for complete search history.

(56) References Cited

U.S. PATENT DOCUMENTS

| 6,384,020 B1 | 5/2002 | Flanner et al. |
| 6,399,828 B1 | 6/2002 | Boswell et al. |
| 7,105,486 B2 | 9/2006 | Mickle et al. |
| 7,223,735 B2 | 5/2007 | Mickle et al. |
| 7,705,184 B2 | 4/2010 | Buenger et al. |
| 2005/0038121 A1 | 2/2005 | Mickle et al. |
| 2005/0208604 A1 | 9/2005 | Zheng et al. |
| 2007/0042955 A1 | 2/2007 | Mickle et al. |
| 2008/0086016 A1 | 4/2008 | Mickle et al. |
| 2011/0196173 A1 | 8/2011 | Meudt et al. |
| 2012/0157706 A1 | 6/2012 | Bauer et al. |

FOREIGN PATENT DOCUMENTS

| DE | 13785 | 9/1957 |
| WO | WO-2008/073918 A1 | 6/2008 |
| WO | WO-2008/098151 A2 | 8/2008 |
| WO | WO-2008/103538 A1 | 8/2008 |

OTHER PUBLICATIONS

Curran, William V. and Boothe, James H. (1978) "The synthesis of deoxynegamycin and some related compounds," *Journal of Antibiotics*, 31(9), pp. 914-918. (abstract only).
International Search Report for International Application No. PCT/US2010/39174, filed Jun. 18, 2010, date of mailing Nov. 15, 2010.
Jass et al. (2003) "Use of N-trifluoroacetyl-protected amino acid chlorides in peptide coupling reactions with virtually complete preservation of stereochemistry," *Tetrahedron*, 59(45), pp. 9019-9029. (abstract only).
Mikhaleva et al. (1980) "Study of the synthesis of α-bungarotoxin. I. Synthesis of a protected heptatriacontapeptide with a sequence (38-74) of α-bungarotoxin," *Bioorganicheskaya Khimiya*, 6(7), pp. 982-1007. (abstract only).
Muller, Horst K. (1956) "Partial asymmetric syntheses of ephedrine derivatives influenced by side-chains and nuclear substituents," *Justus Liebigs Annalen der Chemie*, vol. 599, pp. 211-221. (abstract only).
Taguchi et al. (1955) "Stereochemistry. IV. Alkanolamines. 4. Regular dl-2,5-diphenyl-4-methyloxazoline: The formation and action of methyl tosylate," *Pharmaceutical Bulletin*, vol. 3, pp. 4-7. (abstract only).
International Preliminary Report on Patentability of the International Searching Authority of International Patent Application No. PCT/US2010/039174, issued on Dec. 20, 2011 (9 pages).
Office Action of U.S. Appl. No. 12/973,453, mailed Jan. 28, 2013.
"Benzyl Chloroformate," in *Handbook of Reagents for Organic Synthesis—Activating Agents and Protecting Groups*; Pearson et al., eds., 1999 John Wiley & Sons, pp. 46-50.
Smith and March, *Advanced Organic Chemistry*, 6th ed. (501-502), 2007.

*Primary Examiner* — Jason M Nolan
*Assistant Examiner* — Po-Chih Chen
(74) *Attorney, Agent, or Firm* — Banner & Witcoff, Ltd.

(57) ABSTRACT

The invention provides methods and compositions for preparing amphetamine conjugates, such as lisdexamfetamine, homoarginine-D-amphetamine, and salts thereof. In one embodiment, the invention provides methods of preparing an amphetamine conjugate from a chloramphetamine intermediate.

24 Claims, No Drawings

US 8,614,346 B2

METHODS AND COMPOSITIONS FOR PREPARATION OF AMPHETAMINE CONJUGATES AND SALTS THEREOF

RELATED APPLICATIONS

This application is a national stage of International (PCT) Patent Application Ser. No. PCT/US2010/039174, filed Jun. 18, 2010, and published under PCT Article 21(2) in English, which claims the benefit of and priority to U.S. Provisional Patent Application Ser. No. 61/218,719, filed Jun. 19, 2009, the contents of which are hereby incorporated by reference.

FIELD OF THE INVENTION

The invention provides methods and compositions for preparing amphetamine conjugates, such as lisdexamfetamine, homoarginine-D-amphetamine, and salts thereof. In one embodiment, the invention provides methods of preparing an amphetamine conjugate from a chloramphetamine intermediate.

BACKGROUND OF THE INVENTION

Lisdexamfetamine dimesylate is approved and marketed in the United States for the treatment of attention-deficit hyperactivity disorder in pediatric patients. The active compound lisdexamfetamine contains D-amphetamine covalently linked to the essential amino acid L-lysine. Controlled release of D-amphetamine, a psychostimulant, occurs following administration of lisdexamfetamine to a patient. The controlled release has been reported to occur through hydrolysis of the amide bond linking D-amphetamine and L-lysine.

A procedure for making lisdexamfetamine hydrochloride is described in U.S. Pat. No. 7,223,735 to Mickle et al. (hereinafter Mickle). The procedure involves reacting D-amphetamine with (S)-2,5-dioxopyrrolidin-1-yl 2,6-bis(tert-butoxycarbonylamino)hexanoate to form a lysine-amphetamine intermediate bearing tert-butylcarbamate protecting groups. This intermediate is treated with hydrochloric acid to remove the tert-butylcarbamate protecting groups and provide lisdexamfetamine as its hydrochloride salt.

The procedure in Mickle for making lisdexamfetamine suffers several drawbacks that are particularly problematic when carrying out large scale reactions, such as manufacturing scale, to prepare lisdexamfetamine. For example, the process described by Mickle uses D-amphetamine as a starting material. D-amphetamine is a volatile liquid and vapor from the compound presents a health hazard to plant personnel involved with handling the compound. In addition, D-amphetamine is considered a schedule II controlled substance by the United States Drug Enforcement Agency. As such, the use of large quantities of this controlled substance requires special licenses, permits, and handling procedures and compliance with government regulatory provisions.

The amphetamine conjugate homoarginine-D-amphetamine has been described for use in the treatment of attention-deficit hyperactivity disorder. See, for example, International Patent Application No. WO 2008/073918. Similar to lisdexamfetamine, controlled release of D-amphetamine occurs following administration of homoarginine-D-amphetamine to a patient. Synthetic procedures for making homoarginine-D-amphetamine are described in International Patent Application No. WO 2008/073918, but the synthetic procedures use the schedule II controlled substance D-amphetamine.

Accordingly, the need exists for new methods and compositions for preparing amphetamine conjugates, such as lisdexamfetamine and homoarginine-D-amphetamine, and, in particular, preparing such compounds in high enantiomeric purity. The invention addresses this need and has other related advantages.

SUMMARY

The invention provides methods and compositions for preparing amphetamine conjugates, such as lisdexamfetamine, homoarginine-D-amphetamine, and salts thereof. The synthetic method provides numerous advantages that are particularly important to a manufacturing scale synthesis of an amphetamine conjugate. One such advantage is that the process utilizes starting materials and synthetic intermediates that have low volatility. Another advantage is that none of the starting materials or synthetic intermediates are characterized as a controlled substance by the United States Drug Enforcement Agency. Further advantages of the synthetic process include providing the amphetamine conjugate, such as lisdexamfetamine, in high enantiomeric purity and free of toxic impurities, providing synthetic intermediates that can be used directly in the next reaction step without isolative purification of the synthetic intermediate, and providing mild reaction conditions that are amenable to large scale manufacturing. Other advantages of the methods and compositions are described below and will be apparent to the skilled artisan upon reading of the description and examples herein.

Accordingly, one aspect of the invention provides a method of preparing an acyl-amphetamine compound. The method comprises:
(a) admixing an acyl-halamphetamine compound of Formula I, a hydrogenation catalyst, and hydrogen gas to provide an acyl-amphetamine compound of Formula II; which acyl-amphetamine compound of Formula II is admixed with a deprotecting agent to provide an acyl-amphetamine compound of Formula III; or
(b) admixing an acyl-halamphetamine compound of Formula I and a deprotecting agent to provide an acyl-halamphetamine compound of Formula IIa; which acyl-halamphetamine compound of Formula IIa is admixed with a hydrogenation catalyst and hydrogen gas to provide an acyl-amphetamine compound of Formula III;
wherein the acyl-halamphetamine compound of Formula I is represented by:

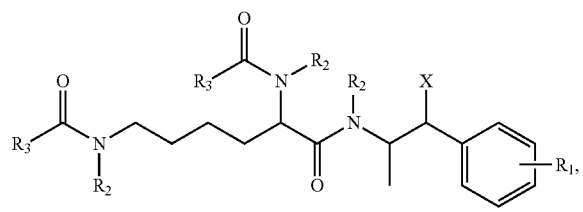

(I)

wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl;
$R_3$ represents independently for each occurrence $C_1$-$C_6$ alkyl, $C_1$-$C_6$ haloalkyl, $C_1$-$C_6$ alkoxy, or aryl; and
X is Cl, Br, or I;
the acyl-amphetamine compound of Formula II is represented by:

(II)

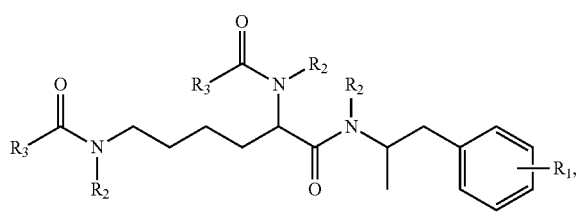

wherein:

$R_1$ is hydrogen, halogen, $C_1$-$C_6$ alkyl, or $C_1$-$C_6$ alkoxy;

$R_2$ represents independently for each occurrence hydrogen or $C_1$-$C_6$ alkyl; and $R_3$ represents independently for each occurrence $C_1$-$C_6$ alkyl, $C_1$-$C_6$ haloalkyl, $C_1$-$C_6$ alkoxy, or aryl;

the acyl-halamphetamine compound of Formula IIa is represented by:

(IIa)

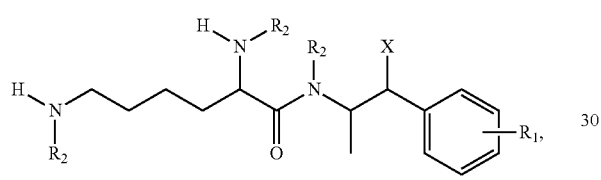

wherein:

$R_1$ is hydrogen, halogen, $C_1$-$C_6$ alkyl, or $C_1$-$C_6$ alkoxy;

$R_2$ represents independently for each occurrence hydrogen or $C_1$-$C_6$ alkyl; and X is Cl, Br, or I; and the acyl-amphetamine compound of Formula III is represented by:

(III)

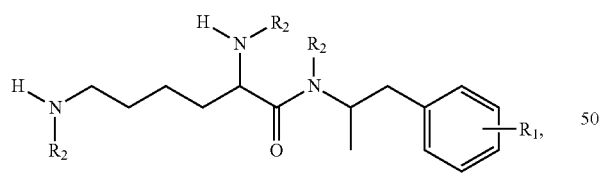

wherein:

$R_1$ is hydrogen, halogen, $C_1$-$C_6$ alkyl, or $C_1$-$C_6$ alkoxy; and $R_2$ represents independently for each occurrence hydrogen or $C_1$-$C_6$ alkyl.

Another aspect of the invention provides a method of preparing an acyl-amphetamine compound. The method comprises admixing an acyl-halamphetamine compound of Formula Ia, a hydrogenation catalyst, and a hydrogen source to provide an acyl-amphetamine compound of Formula III, wherein the acyl-halamphetamine compound of Formula Ia is represented by:

(Ia)

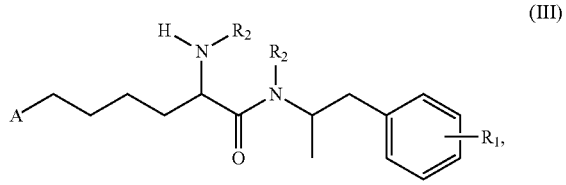

wherein:

A is

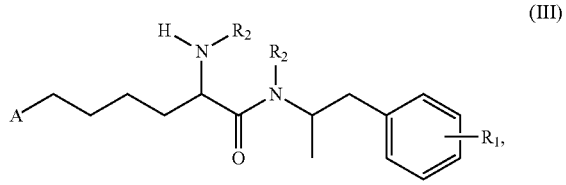

Pg is a protecting group that undergoes deprotection under hydrogenation conditions;

$R_1$ is hydrogen, halogen, $C_1$-$C_6$ alkyl, or $C_1$-$C_6$ alkoxy;

$R_2$ represents independently for each occurrence hydrogen or $C_1$-$C_6$ alkyl;

$R_3$ is, independently for each occurrence, absent, hydrogen, or Pg, in accordance with the rules of valence and provided that one occurrence of $R_3$ is hydrogen, another occurrence of $R_3$ is absent, and the remaining occurrence of $R_3$ is Pg; and X is Cl, Br, or I; and wherein the acyl-amphetamine compound of Formula III is represented by:

(III)

wherein:

$R_1$ is hydrogen, halogen, $C_1$-$C_6$ alkyl, or $C_1$-$C_6$ alkoxy;

$R_2$ represents independently for each occurrence hydrogen or $C_1$-$C_6$ alkyl;

A is —N(H)$R_2$ or

Another aspect of the invention provides compounds that are valuable intermediates in the synthesis of amphetamine conjugate compounds. In certain embodiments, the invention provides a compound of Formula I, Ia, or II, wherein Formula I is represented by:

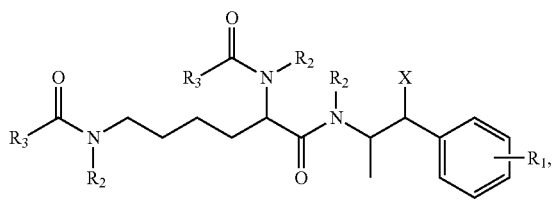

(I)

wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl;
$R_3$ represents independently for each occurrence $C_1$-$C_6$ alkyl, $C_1$-$C_6$ haloalkyl, $C_1$-$C_6$ alkoxy, or aryl; and
X is Cl, Br, or I;

Formula Ia is represented by:

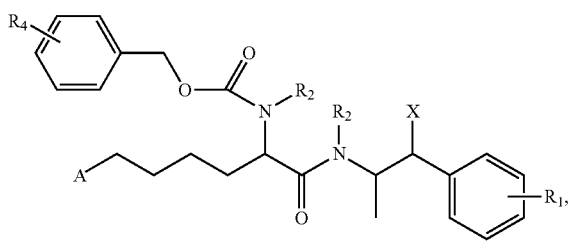

(Ia)

wherein:
A is $R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl;
$R_3$ is, independently for each occurrence, absent, hydrogen, or

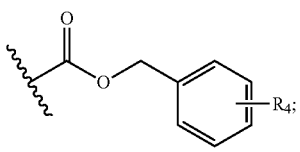

in accordance with the rules of valence and provided that one occurrence of $R_3$ is hydrogen, another occurrence of $R_3$ is absent, and the remaining occurrence of $R_3$ is and
$R_4$ represents independently for each occurrence hydrogen, $C_1$-$C_6$ alkyl, halogen, $C_1$-$C_6$ haloalkyl, or $C_1$-$C_6$ alkoxy;
X is Cl, Br, or I; and Formula II is represented by:

(II)

wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl; and
$R_3$ represents independently for each occurrence $C_1$-$C_6$ haloalkyl.

DETAILED DESCRIPTION OF THE INVENTION

The invention provides methods and compositions for preparing amphetamine conjugates, such as lisdexamfetamine, homoarginine-D-amphetamine, and salts thereof. The synthetic methods provide numerous advantages that are particularly important to a manufacturing scale synthesis of amphetamine conjugates. The practice of the invention employs, unless otherwise indicated, conventional techniques of organic chemistry, such as described in "Comprehensive Organic Synthesis" (B. M. Trost & I. Fleming, eds., 1991-1992). Various aspects of the invention are described below.

I. Description of the Overall Synthesis of Lisdexamfetamine and Related Compounds Exemplary methods for preparing lisdexamfetamine (LDX) and related compounds are described below in the synthetic schemes and accompanying description. In particular, the overall synthetic strategy for preparing lisdexamfetamine dimesylate is shown in Scheme 1. This strategy uses L-lysine and L-norephedrine starting materials, both of which are commercially available. The L-lysine is converted to intermediate B for amide coupling with chloramphetamine compound C. A variety of protecting groups (Pg) on lysine intermediate A are contemplated to be amenable to the present synthetic strategy. See, for example, Greene, T. W.; Wuts, P. G. M. *Protective Groups in Organic Synthesis*, $2^{nd}$ ed.; Wiley: New York, 1991 for a general description of protecting groups. Particularly preferred protecting groups are trifluoroacetyl and benzyloxycarbonyl. Chloramphetamine compound C can be prepared by treating L-norephedrine with thionyl chloride. The chlorination reaction provides compound C in high enantiomeric purity in the form of a hydrochloride salt.

formed efficiently over two steps—one step involves base-catalyzed deprotection of the amino groups, and the other step involves reductive dechlorination of the benzyl chloride through, for example, hydrogenation in the presence of a palladium catalyst.

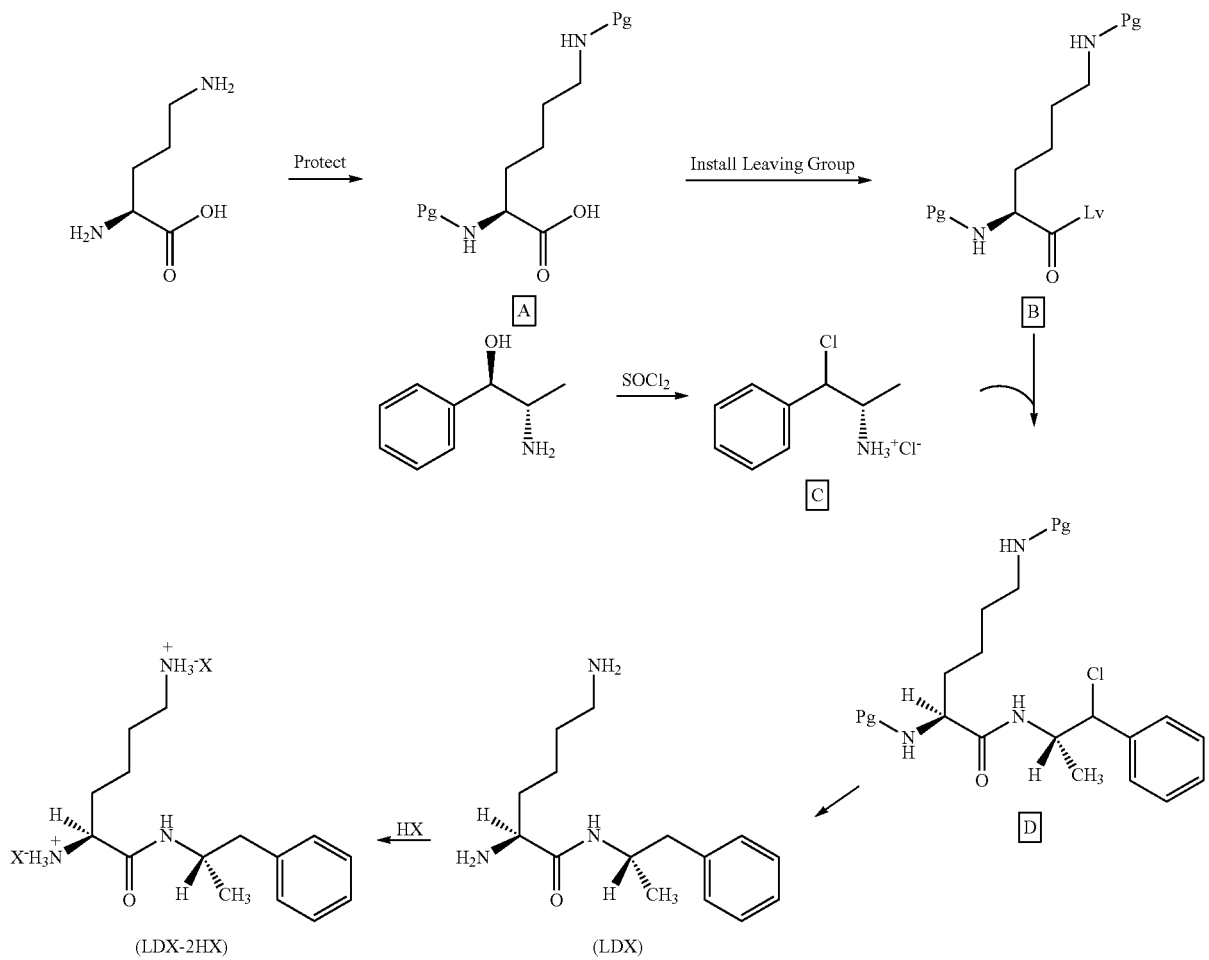

Amide coupling of chloramphetamine compound C and lysine intermediate B can be carried out using a variety of different leaving groups. Particularly preferred leaving groups include chloro and N-hydroxysuccinimidyl. Because chloramphetamine compound C is used in the form of a hydrochloride salt it is preferable to perform the amide coupling procedure in a biphasic solvent system, such as a solvent system containing a mixture of water and an aliphatic acetate.

The next phase of the synthetic procedure involves reductive dechlorination and removal of the amino protecting groups from lysine-amphetamine intermediate D. These synthetic transformations can be performed in a single step or over multiple steps depending on the identity of the protecting groups. For example, when the protecting groups are benzyloxycarbonyl groups, hydrogenation in the presence of a palladium catalyst (e.g., Pd/C) can be used to remove the protecting groups and carry out the reductive dechlorination of the benzyl chloride. Alternatively, when the protecting groups are an acyl group (e.g., trifluoroacetyl), transformation of lysine-amphetamine intermediate D to LDX can be per- Salt forms of LDX can be prepared by reacting LDX with the desired acid. For example, the dimesylate salt of LDX can be prepared by reacting LDX with methanesulfonic acid.

The synthetic procedures outlined above, and described in more detail below, provide numerous advantages that are particularly important to a manufacturing scale synthesis of lisdexamfetamine. One advantage is that the process utilizes starting materials and synthetic intermediates that have low volatility. For example, the synthetic process accommodates using chloramphetamine compound C in the form of a hydrochloride salt, which has a low vapor pressure. This simplifies handling of large quantities of the compound used in the manufacturing process and minimizes the health hazard to plant personnel often associated with using volatile compounds.

Another advantage is that the synthetic process does not use starting materials or synthetic intermediates that are characterized as a controlled substance by the United States Drug Enforcement Agency. Use of a controlled substance in a manufacturing process is preferably avoided due to the health risks posed to plant personnel in handling large quantities of the controlled substance and the costs associated with compliance with regulatory requirements.

Further advantages of the synthetic process include providing the lisdexamfetamine in high enantiomeric purity and free of toxic impurities, and providing synthetic intermediates that can be used directly in the next reaction step without costly or time-consuming purification of the synthetic intermediate. A synthetic process that provides lisdexamfetamine dimesylate in high enantiomeric purity is important because the therapeutic agent approved for treatment of attention-deficit hyperactivity disorder is a single enantiomer. Accordingly, a manufacturing process to supply the drug must be able to provide lisdexamfetamine dimesylate in high enantiomeric purity.

The procedure illustrated in Scheme 1 achieves high enantiomeric purity through a combination of features. One aspect of the synthesis that contributes to the high enantiomeric purity of the final product is that the synthesis uses starting material (i.e., L-lysine and L-norephedrine) of high enantiomeric purity. Another aspect of the synthesis that contributes to the high enantiomeric purity of the final product is that certain intermediates are crystalline solids (e.g., chloramphetamine compound C in Scheme 1 and LDX-(TFA)$_2$ in Scheme 4), and it is possible to isolate the desired enantiomer through selective crystallization. A further aspect of the synthesis that contributes to the high enantiomeric purity of the final product is the mild reaction conditions developed and described herein.

Another advantage is that the synthetic process provides a procedure for preparing a dimesylate salt of LDX that is free of toxic impurities. For example, it is appreciated that the solvent used when reacting LDX with methanesulfonic acid can be important in avoiding undesired generation of potentially toxic impurities. Specifically, it is appreciated that certain alcohol compounds can react with methanesulfonic acid to produce potentially toxic mesylate ethers, and, therefore, the solvent preferably does not contain an alcohol. To address this problem, the synthetic process provides a method of making a dimesylate salt of LDX by performing the salt-forming reaction in an ethereal solvent. This approach provides the dimesylate salt of LDX free of potentially toxic mesylate ethers.

Other advantages of the methods and compositions are described below and will be apparent to the skilled artisan upon reading of the description and examples herein. Particular aspects of the synthetic procedure outlined in Scheme 1 are described in more detail below and further illustrated in Schemes 2-6.

Scheme 2 illustrates preparation of N,N'-bistrifluoro-acetyl-L-lysine (L-LYS-(TFA)$_2$) from L-lysine hydrochloride. The procedure involves treating L-lysine hydrochloride (commercially available) with a base (such as an alkali metal alkoxide, e.g., potassium methoxide) and then adding ethyl trifluoroacetate. The reaction is preferably performed at temperature of about 40° C., and the trifluoroacetyl-protected product can be isolated by adding hydrochloric acid to the reaction solution, filtering the reaction solution to remove particulates, and concentrating the resultant solution to provide L-LYS-(TFA)$_2$ in a form that can be used directly in the next reaction. For additional information, see, for example, Jass et al. (2003) Tetrahedron 59(45): 9019.

SCHEME 2

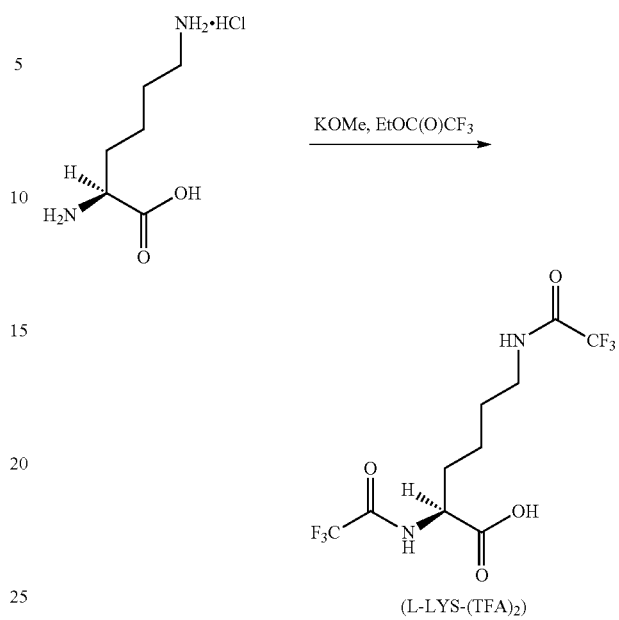

Scheme 3 illustrates preparation of N,N'-bistrifluoro-acetyl-chloro-lisdexamfetamine (Cl-LDX-(TFA)$_2$). The procedure involves converting the carboxylic acid group in protected lysine compound L-LYS-(TFA)$_2$ to an activated acyl group that is more suited for amide coupling. Suitable functional groups include an acid chloride or N-hydroxysuccin-imide ester. Scheme 3 illustrates treating L-LYS-(TFA)$_2$ with Vilsmeier Reagent in order to convert the carboxylic acid group to an acid chloride for amide coupling with chloro-D-amphetamine hydrochloride in the second step. The acid chloride can alternatively be prepared by reacting the carboxylic acid with thionyl chloride, oxalyl chloride, phosphorous trichloride, or phosphorous pentachloride.

In certain instances, the chloro-D-amphetamine hydrochloride is admixed with water and a mild base, such as an alkali metal bicarbonate, e.g., potassium bicarbonate. The process typically provides the chloro-lisdexamfetamine compound Cl-LDX-(TFA)$_2$ in high yield, e.g., greater than about 90%. Another advantage of this reaction procedure is that upon separation of any aqueous layer from the reaction mixture, the resultant organic solution containing the product can be used directly in a subsequent hydrogenation reaction (Scheme 4).

SCHEME 3

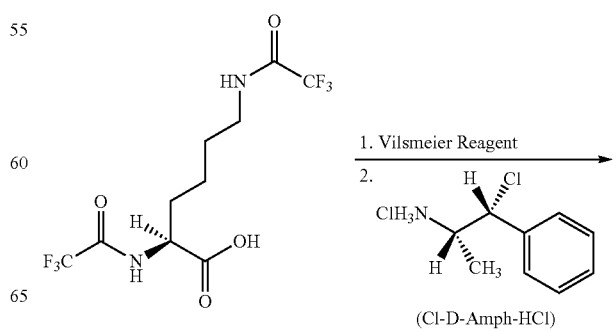

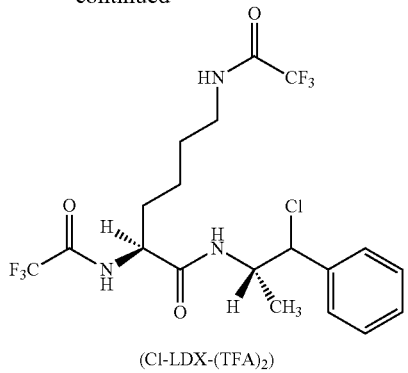

(Cl-LDX-(TFA)₂)

Scheme 4 illustrates preparation of N,N'-bistrifluoro-acetyl-lisdexamfetamine (LDX-(TFA)₂). The procedure involves hydrogenation at mild temperature and pressure in the presence of a palladium catalyst (e.g., Pd/C) in a buffered organic solvent, such as an acetic acid/sodium acetate solvent. In certain instances, the reaction product can be isolated as a powder containing at least some water (e.g., about 15% (w/w), 20% (w/w), 25% (w/w), 30% (w/w), or 40% (w/w), or the powder contains water in the range of up to about 40% (w/w)) in order to facilitate easy handling of the material and avoid delay and expense associated with drying the product to remove water. Further, in certain instances, the enantiomeric purity of the LDX-(TFA)₂ product can be increased by selective crystallization of the compound from aqueous acetic acid.

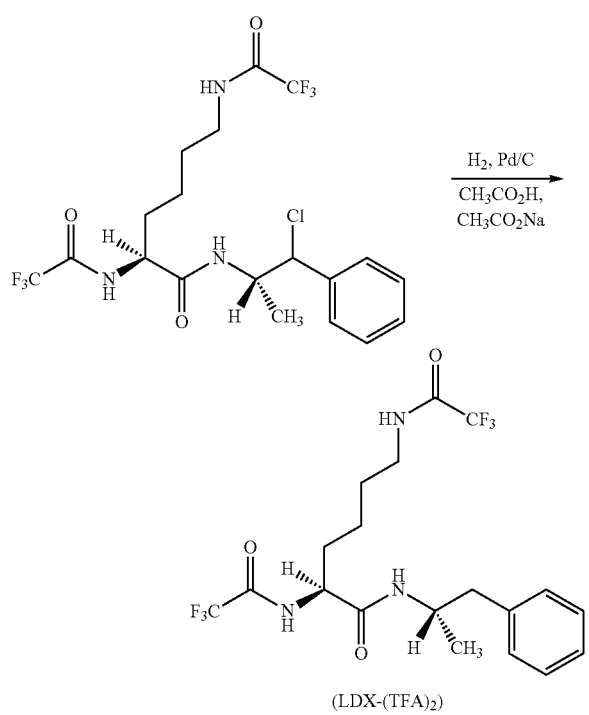

Scheme 5 illustrates preparation of lisdexamfetamine (LDX). The procedure involves removing the protecting groups from LDX-(TFA)₂ generated in the previous step (see Scheme 4). One option for removing the trifluoroacetyl groups is base-catalyzed hydrolysis in a protic solvent, such as an alkali metal hydroxide (e.g., sodium hydroxide) and water. In certain instances, the deprotection reaction is performed using water as the solvent, then once the reaction is finished, the reaction mixture is diluted with an alkyl tetrahydrofuran (e.g., 2-methyl tetrahydrofuran). The aqueous layer from the resulting mixture is discarded, and the organic layer may be washed one or more times with water. Then, in certain instances, a filter aid (e.g., Celatom) is added to the organic solvent/LDX mixture and the resulting mixture is filtered. The filtrate can be concentrated to provide LDX, or the filtrate can be used directly in a subsequent reaction to form a salt of LDX. The use of 2-methyl tetrahydrofuran permits isolating LDX that is substantially free of sodium (e.g., less than 5% (w/w), 2% (w/w) or 1% (w/w)).

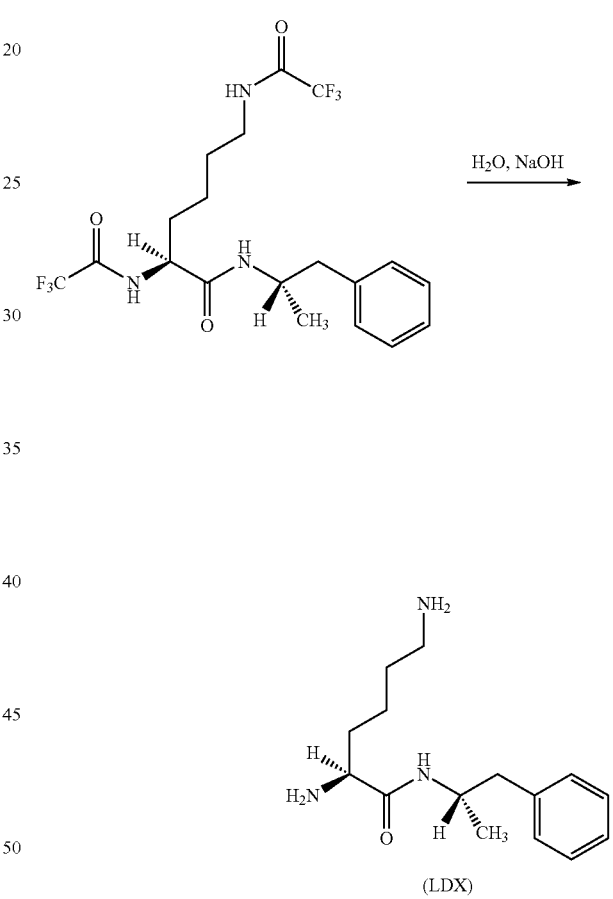

Scheme 6 illustrates preparation of lisdexamfetamine dimesylate (LDX-2MSA). The procedure involves reacting LDX with methanesulfonic acid. It is contemplated that other acid salts of LDX can be prepared using a similar procedure by substituting another acid (e.g., HCl, HBr, and the like) for methanesulfonic acid. As explained above, it is preferable in certain embodiments to use an ethereal solvent when reacting LDX with methanesulfonic acid. It is appreciated that certain alcohol compounds can react with methanesulfonic acid to produce potentially toxic mesylate ethers. The use of ethereal solvents (e.g., dialkyl ethers such as dimethyl ether, tert-butyl methyl ether and the like) generally avoids production of potentially toxic mesylate ethers, thereby providing the dimesylate salt of LDX free of such potentially toxic impurities.

SCHEME 6

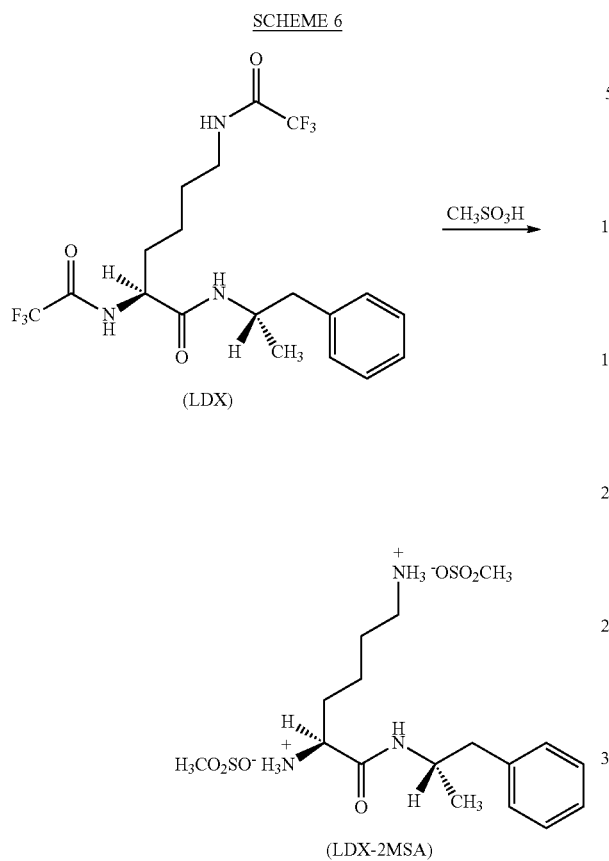

(LDX)

(LDX-2MSA)

Scheme 7 illustrates preparation of chloro-D-amphetamine hydrochloride (Cl-D-Amph-HCl), which is used as starting material for the synthesis of LDX. The procedure involves reacting L-norephedrine with thionyl chloride to provide the title compound as a solid.

SCHEME 7

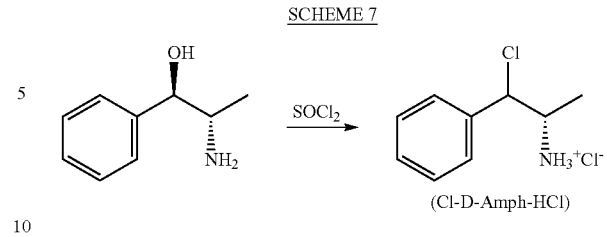

(Cl-D-Amph-HCl)

In certain embodiments, the solvent used in the chlorination reaction is toluene. Toluene is advantageous over benzene or chloroform in that the Cl-D-Amph-HCl product tends to be less soluble (i.e., more insoluble) in toluene, particularly below ambient temperatures. Thus, the Cl-D-Amph-HCl product precipitates readily from the reaction mixture making it convenient to isolate by filtration. In certain embodiments, the filter cake containing the Cl-D-Amph-HCl product is washed with additional solvent, preferably toluene, to remove any residual impurities.

If additional purification of Cl-D-Amph-HCl is desired, then the Cl-D-Amph-HCl product can be dissolved in purified water and contacted with carbon (e.g., active carbon). Contacting can be accomplished by filtering the aqueous solution of the crude Cl-D-Amph-HCl through a bed of carbon. In this approach, the carbon, in a particulate form, is usually retained on a filter. Preferably, the filter bed also includes some diatomaceous earth (e.g., Celatom). The bed of solids (including the carbon and the diatomaceous earth) retained on the filter is washed with additional water, and the Cl-D-Amph-HCl is used directly as an aqueous solution or isolated from the recovered filtrates.

II. Description of the Overall Synthesis of Homoarginine-D-Amphetamine and Related Compounds Exemplary methods for preparing homoarginine-D-amphetamine and related compounds are described below in the synthetic schemes and accompanying description. In particular, the overall synthetic strategy for preparing homoarginine-D-amphetamine dihydrochloride is shown in Scheme 8.

SCHEME 8

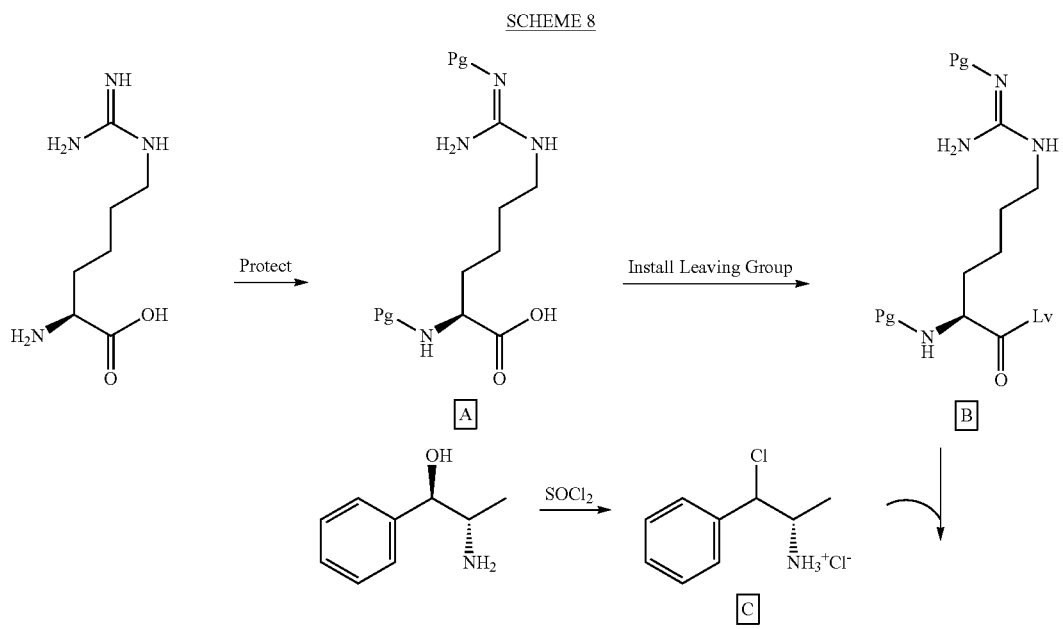

-continued

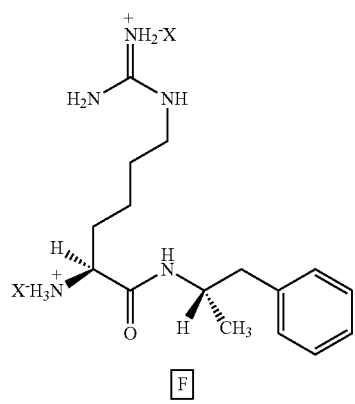

F

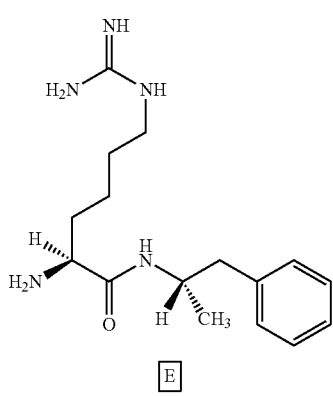

E

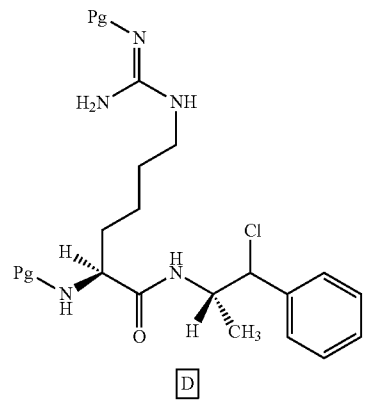

D

The strategy depicted in Scheme 8 uses homoarginine and L-norephedrine starting materials, both of which are commercially available. The homoarginine is converted to intermediate B for amide coupling with chloramphetamine compound C. A variety of protecting groups (Pg) on homoarginine intermediate A are contemplated to be amenable to the present synthetic strategy. See, for example, Greene, T. W.; Wuts, P. G. M. *Protective Groups in Organic Synthesis*, $2^{nd}$ ed.; Wiley: New York, 1991 for a general description of protecting groups. One particularly preferred protecting group for use in protecting the guanidine moiety is a nitro group. Chloramphetamine compound C can be prepared by treating L-norephedrine with thionyl chloride. The chlorination reaction provides compound C in high enantiomeric purity in the form of a hydrochloride salt.

Amide coupling of chloramphetamine compound C and protected homoarginine intermediate B can be carried out using a variety of different leaving groups. Particularly preferred leaving groups include chloro and N-hydroxysuccinimidyl. Because chloramphetamine compound C is in the form of a hydrochloride salt it is preferable, in certain instances, to mix chloramphetamine compound C with a base (e.g., sodium carbonate or sodium bicarbonate in a solvent, such as water) to provide the free base of compound C, which is then reacted with protected homoarginine intermediate B to provide homoarginine-amphetamine intermediate D.

The next phase of the synthetic procedure involves reductive dechlorination and removal of the protecting groups from homoarginine-amphetamine intermediate D. This synthetic transformation can be performed in a single step when the protecting groups are benzyloxycarbonyl groups and nitro groups by hydrogenation in the presence of a palladium catalyst (e.g., Pd/C).

Salt forms of compound E can be prepared by reacting compound E with an acid, such as hydrochloric acid.

The synthetic procedures outlined above, and described in more detail below, provide numerous advantages that are particularly important to a manufacturing scale synthesis of homoarginine-D-amphetamine. One advantage is that the process utilizes starting materials and synthetic intermediates that have low volatility. This simplifies handling of large quantities of the compound used in the manufacturing process and minimizes the health hazard to plant personnel often associated with using volatile compounds. Another advantage is that the synthetic process does not use starting materials or synthetic intermediates that are characterized as a controlled substance by the United States Drug Enforcement Agency. Use of a controlled substance in a manufacturing process is preferably avoided due to the health risks posed to plant personnel in handling large quantities of the controlled substance and the costs associated with compliance with regulatory requirements.

Other advantages of the methods and compositions are described below and will be apparent to the skilled artisan upon reading of the description and examples herein. Particular aspects of the synthetic procedure outlined in Scheme 8 are described in more detail below and further illustrated in Schemes 9 and 10.

Scheme 9 illustrates preparation of protected homoarginine-D-chloro-amphetamine. The procedure involves admixing D-chloramphetamine hydrochloride with a mild base (such as an alkali metal carbonate or bicarbonate, e.g., sodium carbonate or sodium bicarbonate) in the presence of a solvent. Exemplary solvents include alkyl acetate compounds (e.g., propyl acetate, ethyl acetate, and butyl acetate), water, and mixtures thereof. Treatment with mild base can be performed at ambient temperature. After the reaction using mild base is complete, any aqueous phase of the reaction mixture can be separated, and the protected homoarginine activated ester can be added. The reaction mixture can be heated if necessary, such as to a temperature in the range of, for example, 20-50° C. After the amide coupling reaction is complete, the protected homoarginine-D-chloramphetamine product can be isolated, such as by diluting the reaction mixture with an alkyl alcohol, heating to a temperature in the range of 40-60° C., then cooling the reaction mixture to a temperature of about 20° C. to provide slurry, and filtering the slurry to provide the protected homoarginine-D-chloramphetamine product.

SCHEME 9

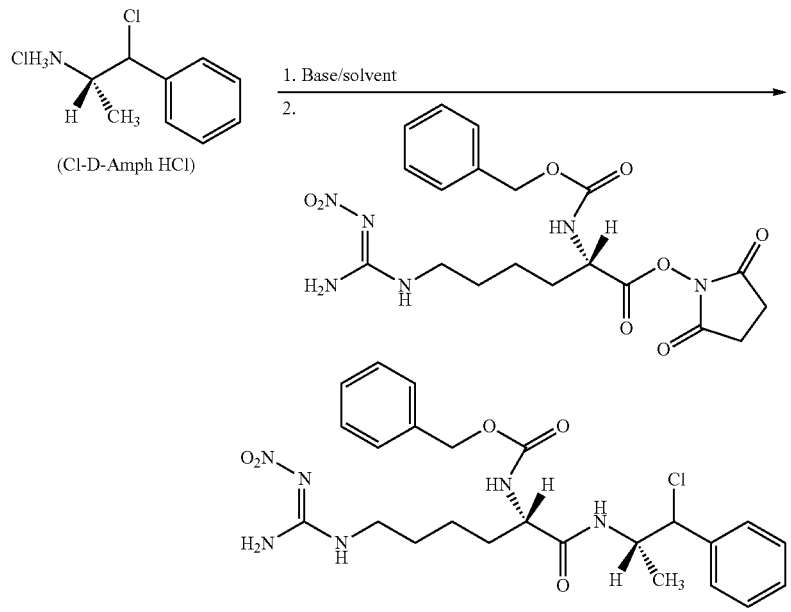

Scheme 10 illustrates a procedure for reductive dechlorination of the protected homoarginine-D-chloramphetamine to provide homoarginine-D-amphetamine dihydrochloride. The reduction reaction can be performed in the presence of a palladium catalyst (e.g., Pd/C) and an alkyl alcohol solvent, such as methanol, ethanol, propanol, butanol (e.g., n-butanol), and the like. Exemplary hydrogen sources for the reduction reaction include hydrogen gas and ammonium formate. In certain instances, it may desirable to heat the reaction mixture to a temperature in the range of 30-70° C. and, once the reaction is complete, filter the hot reaction mixture. The filtrate can be used directly to prepare a salt of homoarginine-D-amphetamine, such as by adding hydrochloride acid to the mixture to provide homoarginine-D-amphetamine dihydrochloride.

SCHEME 10

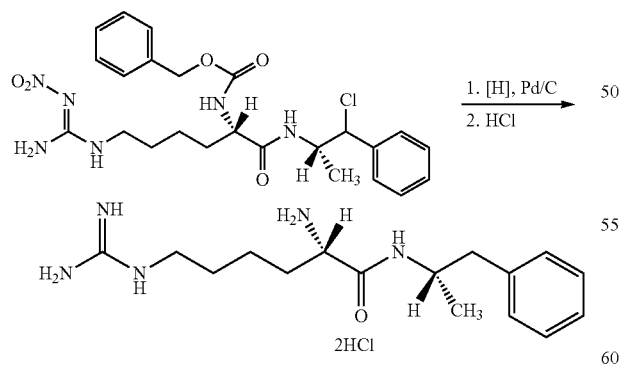

III. Description of Preferred Aspects of the Synthesis of Amphetamine Conjugates One aspect of the invention provides a method of preparing an acyl-amphetamine compound, comprising:

(a) admixing an acyl-halamphetamine compound of Formula I, a hydrogenation catalyst, and a hydrogen source, e.g., hydrogen gas, to provide an acyl-amphetamine compound of Formula II; which acyl-amphetamine compound of Formula II is admixed with a deprotecting agent to provide an acyl-amphetamine compound of Formula III; or (b) admixing an acyl-halamphetamine compound of Formula I and a deprotecting agent to provide an acyl-halamphetamine compound of Formula IIa; which acyl-halamphetamine compound of Formula IIa is admixed with a hydrogenation catalyst and a hydrogen source, e.g., hydrogen gas, to provide an acyl-amphetamine compound of Formula III;

wherein the acyl-halamphetamine compound of Formula I is represented by:

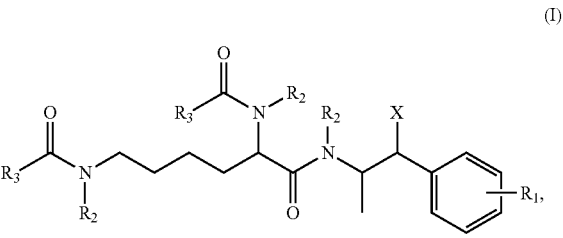

(I)

wherein:

$R_1$ is hydrogen, halogen, $C_1$-$C_6$ alkyl, or $C_1$-$C_6$ alkoxy;

$R_2$ represents independently for each occurrence hydrogen or $C_1$-$C_6$ alkyl;

$R_3$ represents independently for each occurrence $C_1$-$C_6$ alkyl, $C_1$-$C_6$ haloalkyl, $C_1$-$C_6$ alkoxy, or aryl; and X is Cl, Br, or I;

wherein the acyl-amphetamine compound of Formula II is represented by:

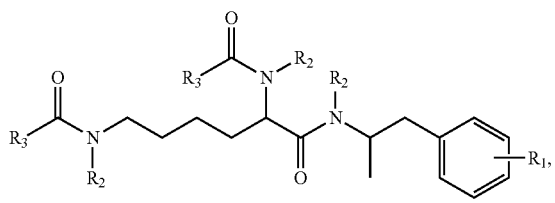

(II)

wherein:
R₁ is hydrogen, halogen, $C_1$-$C_6$ alkyl, or $C_1$-$C_6$ alkoxy;
R₂ represents independently for each occurrence hydrogen or $C_1$-$C_6$ alkyl; and
R₃ represents independently for each occurrence $C_1$-$C_6$ alkyl, $C_1$-$C_6$ haloalkyl, $C_1$-$C_6$ alkoxy, or aryl;
the acyl-halamphetamine compound of Formula IIa is represented by:

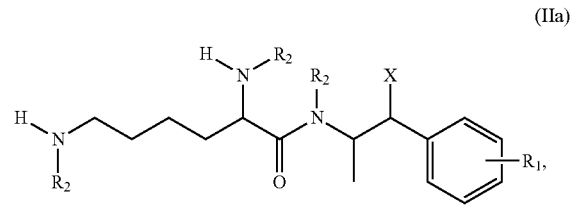

(IIa)

wherein:
R₁ is hydrogen, halogen, $C_1$-$C_6$ alkyl, or $C_1$-$C_6$ alkoxy;
R₂ represents independently for each occurrence hydrogen or $C_1$-$C_6$ alkyl; and
X is Cl, Br, or I; and
the acyl-amphetamine compound of Formula III is represented by:

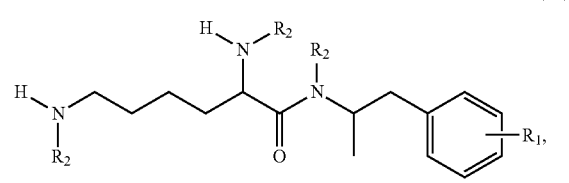

(III)

wherein:
R₁ is hydrogen, halogen, $C_1$-$C_6$ alkyl, or $C_1$-$C_6$ alkoxy; and
R₂ represents independently for each occurrence hydrogen or $C_1$-$C_6$ alkyl.

In certain embodiments, R₁ is hydrogen. In certain embodiments, R₂ is hydrogen. In certain embodiments, R₃ is $C_1$-$C_6$ haloalkyl. In certain embodiments, R₃ is $C_1$-$C_6$ alkyl, $C_1$-$C_6$ haloalkyl, or aryl. In certain embodiments, R₃ is trifluoromethyl. In certain embodiments, the hydrogenation catalyst comprises palladium. In certain embodiments, the hydrogenation catalyst comprises palladium on carbon. In certain embodiments, the step requiring admixing a hydrogenation catalyst and a hydrogen source (e.g., hydrogen gas) further comprises admixing acetic acid. In certain embodiments, the step requiring admixing a hydrogenation catalyst and a hydrogen source (e.g., hydrogen gas) further comprises admixing acetic acid and an alkali metal ethanoate. In certain embodiments, the method further comprises isolating the acyl-amphetamine compound of Formula II as a solid comprising from about 15% (w/w) to about 40% (w/w) water. In certain embodiments, the deprotecting agent comprises a base and the compound R₄—OH, wherein R₄ is hydrogen, $C_1$-$C_6$ alkyl, or aryl. In certain embodiments, the base is an alkali metal hydroxide. In certain embodiments, the deprotecting agent is a mixture of sodium hydroxide and water.

In certain embodiments, the method comprises admixing an acyl-halamphetamine compound of Formula I, a hydrogenation catalyst, and hydrogen gas to provide an acyl-amphetamine compound of Formula II; which acyl-amphetamine compound of Formula II is admixed with a deprotecting agent to provide an acyl-amphetamine compound of Formula III.

In certain embodiments, the method further comprises crystallizing the acyl-amphetamine compound of Formula II from a mixture comprising acetic acid and water.

In certain embodiments, wherein after the acyl-amphetamine compound of Formula II is admixed with a deprotecting agent to provide an acyl-amphetamine compound of Formula III, the method further comprises admixing an alkyl tetrahydrofuran and isolating the acyl-amphetamine compound of Formula III.

In certain embodiments, after the deprotection reaction is at least 90% complete, the method further comprises admixing Celatom and filtering the reaction solution and isolating the filtrate containing the acyl-amphetamine compound of Formula III.

In certain other embodiments, deprotection reaction is performed in an aqueous solvent and after the deprotection reaction is at least 90% complete, the method further comprises admixing an alkyl tetrahydrofuran (e.g., 2-methyl tetrahydrofuran or 2-ethyl tetrahydrofuran) and isolating the acyl-amphetamine compound of Formula III.

In certain embodiments, the acyl-halamphetamine compound of Formula I is represented by:

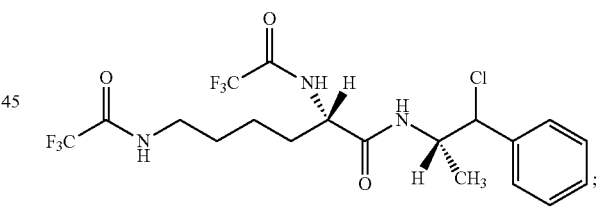

the acyl-amphetamine compound of Formula II is represented by:

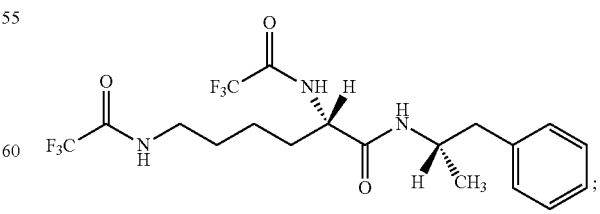

and
the acyl-amphetamine compound of Formula III is represented by:

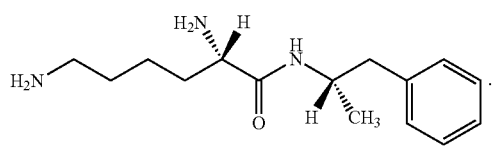 [SMILES: C[C@@H](Cc1ccccc1)NC(=O)[C@@H](N)CCCCN]

In certain other embodiments, the acyl-halamphetamine compound of Formula I is represented by:

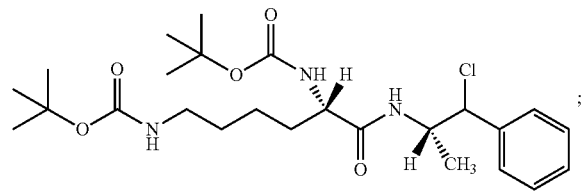 [SMILES: C[C@H](NC(=O)[C@H](CCCCNC(=O)OC(C)(C)C)NC(=O)OC(C)(C)C)C(Cl)c1ccccc1]

the acyl-amphetamine compound of Formula II is represented by:

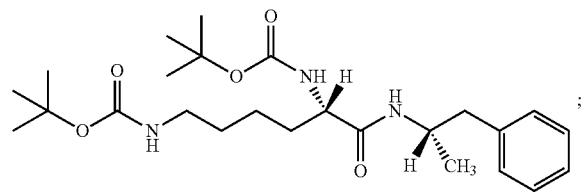 [SMILES: C[C@@H](Cc1ccccc1)NC(=O)[C@H](CCCCNC(=O)OC(C)(C)C)NC(=O)OC(C)(C)C]

and the acyl-amphetamine compound of Formula III is represented by:

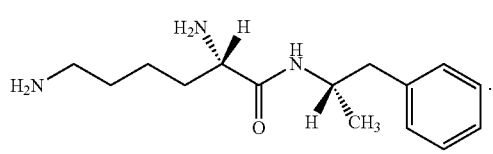 [SMILES: C[C@@H](Cc1ccccc1)NC(=O)[C@@H](N)CCCCN]

Another aspect of the invention provides a method of preparing an acyl-amphetamine compound, comprising admixing an acyl-halamphetamine compound of Formula Ia, a hydrogenation catalyst, and a hydrogen source to provide an acyl-amphetamine compound of Formula III, wherein the acyl-halamphetamine compound of Formula Ia is represented by:

(Ia)

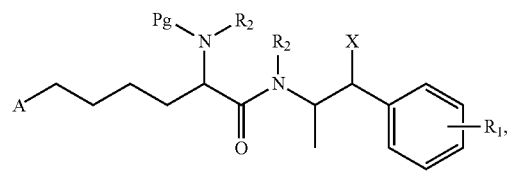

wherein:
A is

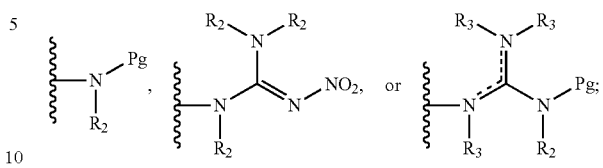

Pg is a protecting group that undergoes deprotection under hydrogenation conditions;
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl;
$R_3$ is, independently for each occurrence, absent, hydrogen, or Pg, in accordance with the rules of valence and provided that one occurrence of $R_3$ is hydrogen, another occurrence of $R_3$ is absent, and the remaining occurrence of $R_3$ is Pg; and
X is Cl, Br, or I and
wherein the acyl-amphetamine compound of Formula III is represented by:

(III)

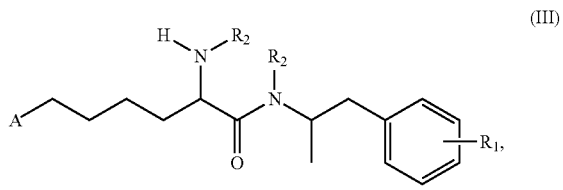

wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl;
A is —N(H)$R_2$ or

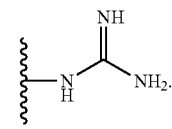

Protecting groups that undergo deprotection under hydrogenation conditions are known in the art. See, for example, Greene, T. W.; Wuts, P. G. M. *Protective Groups in Organic Synthesis*, $2^{nd}$ ed.; Wiley: New York, 1991. In certain embodiments, Pg is

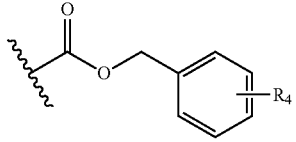

wherein $R_4$ represents independently for each occurrence hydrogen, $C_1$-$C_6$ alkyl, halogen, $C_1$-$C_6$ haloalkyl, or $C_1$-$C_6$ alkoxy. In certain other embodiments, Pg is —C(O)OCH$_2$—Ar, wherein Ar is phenyl optionally substituted with one or more substituents independently selected from the group consisting of halogen, nitro, —OC(O)-alkyl, —OC(O)-aryl, boronate ester, alkoxy, and alkyl. In certain other embodiments, Pg is one of the following:

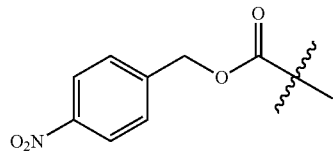

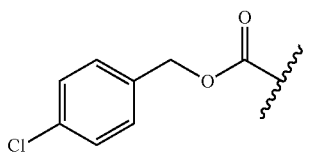

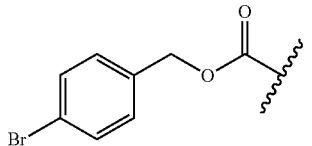

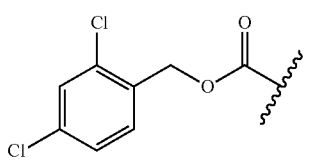

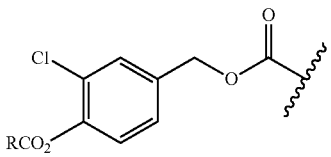

R is alkyl, aryl, or aralkyl

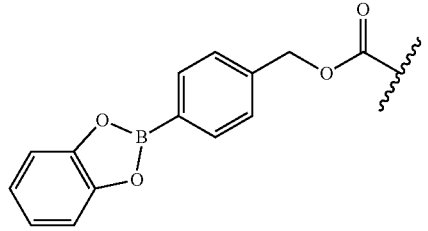

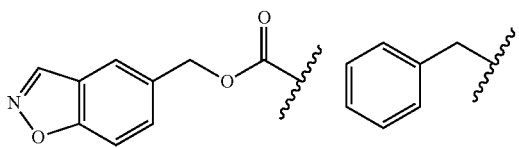

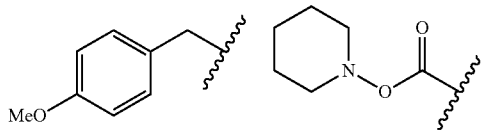

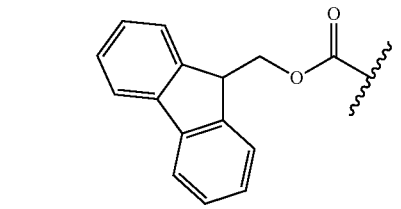

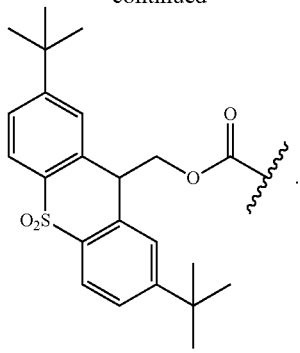

In certain embodiments, $R_1$ is hydrogen. In certain embodiments, $R_2$ is hydrogen. In certain embodiments, $R_3$ is hydrogen. In certain embodiments, variable A in formula Ia is

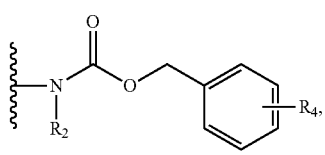

wherein $R_4$ is hydrogen, $C_1$-$C_6$ alkyl, halogen, $C_1$-$C_6$ haloalkyl, or $C_1$-$C_6$ alkoxy. In certain other embodiments, variable A in formula Ia is

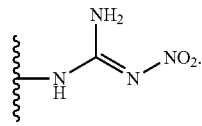

In certain other embodiments, variable A in formula Ia is

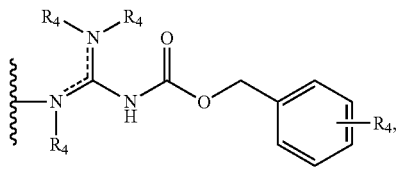

wherein $R_4$ is hydrogen, $C_1$-$C_6$ alkyl, halogen, $C_1$-$C_6$ haloalkyl, or $C_1$-$C_6$ alkoxy. In certain other embodiments, variable A in formula Ia is

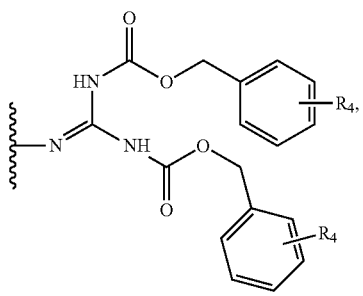

wherein R₄ is hydrogen, $C_1$-$C_6$ alkyl, halogen, $C_1$-$C_6$ haloalkyl, or $C_1$-$C_6$ alkoxy.

In certain embodiments, the acyl-halamphetamine compound of Formula Ia is represented by:

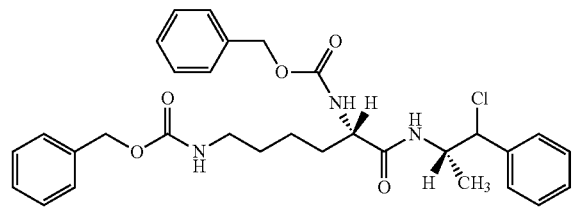

and the acyl-amphetamine compound of Formula III is represented by:

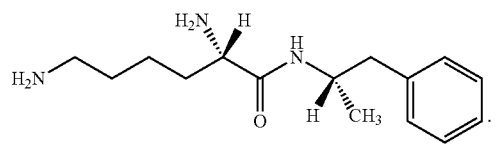 [SMILES: C[C@@H](Cc1ccccc1)NC(=O)[C@@H](N)CCCCN]

In other certain embodiments, the acyl-halamphetamine compound of Formula Ia is represented by:

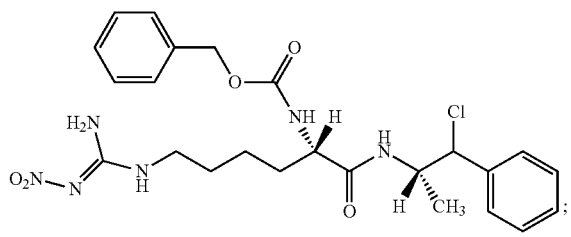 [SMILES: C[C@H](NC(=O)[C@H](CCCCN/C(N)=N/[N+](=O)[O-])NC(=O)OCc1ccccc1)C(Cl)c1ccccc1]

and the acyl-amphetamine compound of Formula III is represented by:

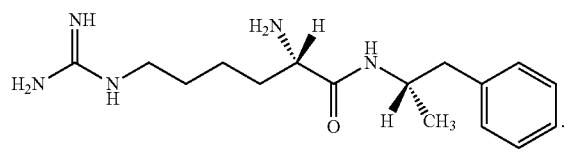 [SMILES: C[C@@H](Cc1ccccc1)NC(=O)[C@@H](N)CCCCNC(=N)N]

In certain embodiments, the hydrogenation catalyst comprises palladium. In certain embodiments, the hydrogenation catalyst comprises palladium on carbon. In certain embodiments, the hydrogen source is hydrogen gas or ammonium formate.

In certain embodiments, the method further comprises admixing acetic acid and an alkali metal ethanoate.

In certain embodiments, the method further comprises admixing a halamphetamine compound of Formula IV and a protected lysine compound of Formula V to provide a compound of Formula I; wherein the halamphetamine compound of Formula IV is represented by:

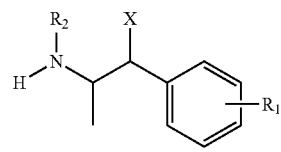

or a salt thereof, wherein:

$R_1$ is hydrogen, halogen, $C_1$-$C_6$ alkyl, or $C_1$-$C_6$ alkoxy;

$R_2$ represents independently for each occurrence hydrogen or $C_1$-$C_6$ alkyl; and X is Cl, Br, or I; and wherein the protected lysine compound of Formula V is represented by:

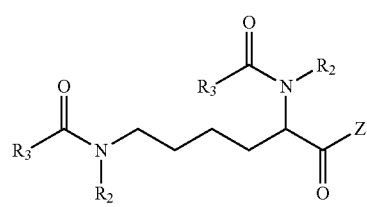

wherein:

$R_2$ represents independently for each occurrence hydrogen or $C_1$-$C_6$ alkyl; and $R_3$ represents independently for each occurrence $C_1$-$C_6$ alkyl, $C_1$-$C_6$ haloalkyl, $C_1$-$C_6$ alkoxy, or aryl; and Z is a leaving group.

In certain embodiments, $R_3$ is $C_1$-$C_6$ alkyl, $C_1$-$C_6$ haloalkyl, or aryl. In certain embodiments, the compound of Formula I is represented by:

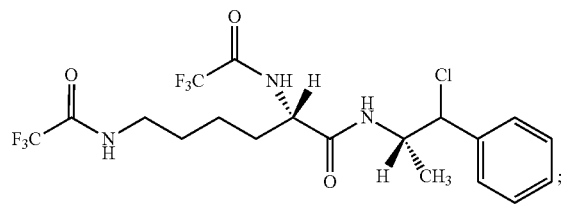

the acyl-amphetamine compound of Formula II is represented by:

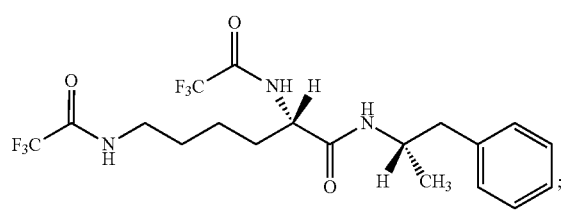 [SMILES: C[C@@H](Cc1ccccc1)NC(=O)[C@H](CCCCNC(=O)C(F)(F)F)NC(=O)C(F)(F)F]

the acyl-halamphetamine compound of Formula IIa is represented by:

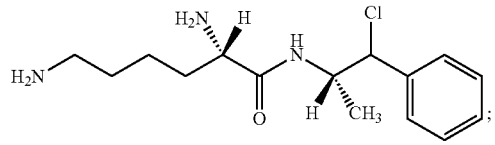 [SMILES: C[C@H](NC(=O)[C@@H](N)CCCCN)C(Cl)c1ccccc1]

the acyl-amphetamine compound of Formula III is represented by:

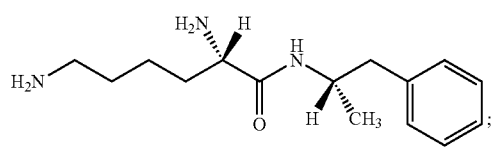 [SMILES: C[C@@H](Cc1ccccc1)NC(=O)[C@@H](N)CCCCN]

the halamphetamine compound of Formula IV is represented by:

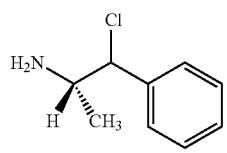

or a hydrochloride salt thereof; and
the protected lysine compound of Formula V is represented by:

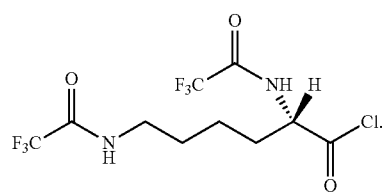 [SMILES: O=C(Cl)[C@H](CCCCNC(=O)C(F)(F)F)NC(=O)C(F)(F)F]

In certain embodiments, the method further comprises admixing a halamphetamine compound of Formula IV and a protected amino compound of Formula Va to provide a compound of Formula Ia; wherein the halamphetamine compound of Formula IV is represented by:

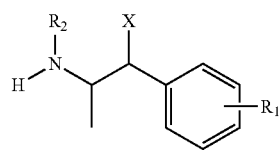

or a salt thereof, wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl; and
X is Cl, Br, or I; and
the protected amino acid compound of Formula Va is represented by:

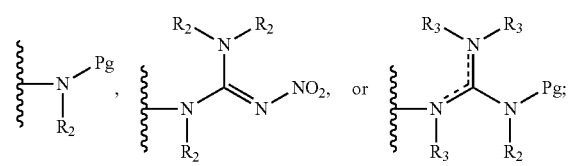

wherein:
A is

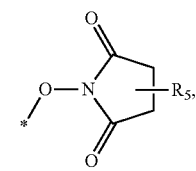

Pg is a protecting group that undergoes deprotection under hydrogenation conditions;
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl;
$R_3$ is, independently for each occurrence, absent, hydrogen, or Pg, in accordance with the rules of valence and provided that one occurrence of $R_3$ is hydrogen, another occurrence of $R_3$ is absent, and the remaining occurrence of $R_3$ is Pg; and
Z is a leaving group.
In certain embodiments, Pg is wherein $R_4$ represents independently for each occurrence hydrogen, $C_1$-$C_6$ alkyl, halogen, $C_1$-$C_6$ haloalkyl, or $C_1$-$C_6$ alkoxy.
In certain embodiments, Z is chloro, bromo, fluoro, iodo, or wherein $R_5$ is hydrogen or $C_1$-$C_6$ alkyl. In certain embodiments, Z is chloro. In certain embodiments, the method further comprises admixing water and alkali metal bicarbonate. In certain embodiments, $R_1$ is hydrogen. In certain embodiments, $R_2$ is hydrogen. In certain embodiments, X is chloro.
In certain embodiments, variable $R_3$ in Formula V is $C_1$-$C_6$ haloalkyl.

In certain embodiments, A is

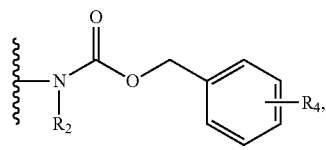

wherein $R_4$ represents independently for each occurrence hydrogen, $C_1$-$C_6$ alkyl, halogen, $C_1$-$C_6$ haloalkyl, or $C_1$-$C_6$ alkoxy. In certain embodiments, A is

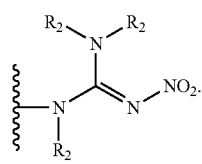

In certain embodiments, A is

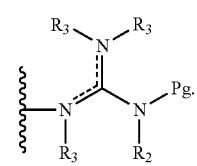

In certain embodiments, the method further comprises admixing a norephedrine compound of Formula VI and a halogenating agent to provide a halamphetamine compound of Formula IV; wherein the halamphetamine compound of Formula IV is represented by:

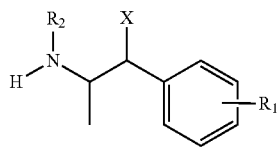

or a salt thereof, wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl; and
X is Cl, Br, or I; and
the norephedrine compound of Formula VI is represented by:

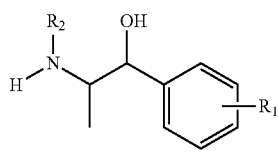

or a salt thereof, wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl; and In certain embodiments, the halogenating reagent is thionyl chloride.

In certain embodiments, the halamphetamine compound of Formula IV is represented by:

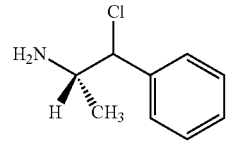

or a hydrochloride salt thereof. In certain embodiments, the norephedrine compound of Formula VI is L-norephedrine.

In certain embodiments, the method further comprises admixing a protected lysine compound of Formula VIII with a carboxylic acid-activating agent to provide a protected lysine compound of Formula V; wherein the protected lysine compound of Formula V is represented by:

(V)

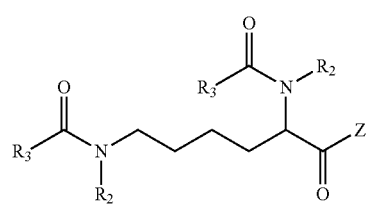

wherein:
Z is a leaving group selected from the group consisting of chloro, bromo, fluoro, iodo, or

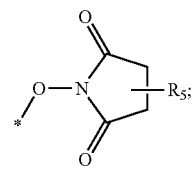

$R_2$ represents independently for each occurrence hydrogen or $C_1$-$C_6$ alkyl;
$R_3$ represents independently for each occurrence $C_1$-$C_6$ alkyl, $C_1$-$C_6$ haloalkyl, $C_1$-$C_6$ alkoxy, or aryl; and
$R_5$ is hydrogen or $C_1$-$C_6$ alkyl; and
the protected lysine compound of Formula VIII is represented by:

(VIII)

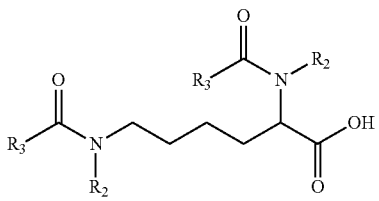

wherein:
R$_2$ represents independently for each occurrence hydrogen or C$_1$-C$_6$ alkyl; and
R$_3$ represents independently for each occurrence C$_1$-C$_6$ alkyl, C$_1$-C$_6$ haloalkyl, C$_1$-C$_6$ alkoxy, or aryl.

In certain embodiments, R$_2$ is hydrogen. In certain embodiments, R$_3$ is C$_1$-C$_6$ alkyl, C$_1$-C$_6$ haloalkyl, or aryl. In certain embodiments, R$_3$ is C$_1$-C$_6$ haloalkyl, such as trifluoromethyl. In certain embodiments, the carboxylic acid-activating agent is Vilsmeier Reagent, thionyl chloride, oxalyl chloride, PCl$_3$, PCl$_5$, or PBr$_3$. In certain embodiments, the carboxylic acid-activating agent comprises cyanuric fluoride, or comprises hydrogen fluoride-pyridine and 1,3-dicyclohexylcarbodiimide, as used in making acyl fluorides. In certain embodiments, the carboxylic acid-activating agent comprises diiodosilane, as used in making acyl iodides. See, for example, Keinan et al. (1990) J. Org. Chem., 55: 3922. In certain embodiments, the carboxylic acid-activating agent is Vilsmeier Reagent or thionyl chloride. In certain embodiments, the carboxylic acid-activating agent is Vilsmeier Reagent.

In certain embodiments, the protected lysine compound of Formula V is represented by:

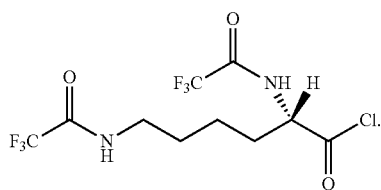 [SMILES: O=C(Cl)[C@H](CCCCNC(=O)C(F)(F)F)NC(=O)C(F)(F)F]

In certain embodiments, the protected lysine compound of Formula VIII is represented by:

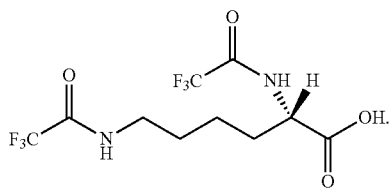 [SMILES: O=C(O)[C@H](CCCCNC(=O)C(F)(F)F)NC(=O)C(F)(F)F]

In certain embodiments, the method further comprises admixing a lysine compound of Formula IX with a protecting group agent to provide a protected lysine compound of Formula VIII; wherein:
the protecting group agent is represented by the formula R$_3$C(O)Y, wherein R$_3$ is C$_1$-C$_6$ alkyl, C$_1$-C$_6$ haloalkyl, C$_1$-C$_6$ alkoxy, or aryl; and Y is C$_1$-C$_6$ alkoxy, —O—C$_1$C$_6$acyl, chloro, bromo, fluoro, or

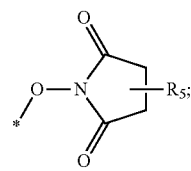

wherein R$_5$ is hydrogen or C$_1$-C$_6$ alkyl;
the protected lysine compound of Formula VIII is represented by:

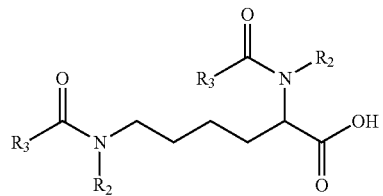

wherein:
R$_2$ represents independently for each occurrence hydrogen or C$_1$-C$_6$ alkyl; and
R$_3$ represents independently for each occurrence C$_1$-C$_6$ alkyl, C$_1$-C$_6$ haloalkyl, C$_1$-C$_6$ alkoxy, or aryl; and
the lysine compound of Formula IX is represented by:

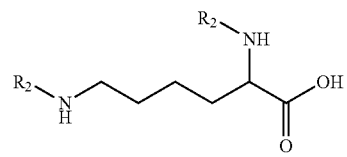

or a salt thereof, wherein:
R$_2$ represents independently for each occurrence hydrogen or C$_1$-C$_6$ alkyl.

In certain embodiments, the method further comprises admixing an acyl-amphetamine compound of Formula III and an acid to provide an acid salt of said acyl-amphetamine compound of Formula III; wherein Formula III is represented by:

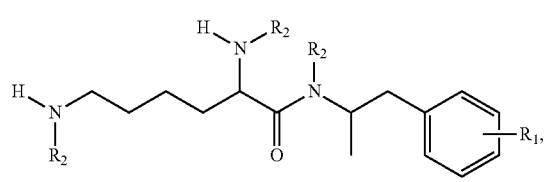

wherein:
R$_1$ is hydrogen, halogen, C$_1$-C$_6$ alkyl, or C$_1$-C$_6$ alkoxy; and
R$_2$ represents independently for each occurrence hydrogen or C$_1$-C$_6$ alkyl.

In certain embodiments, the acid is an organic acid or a mineral acid. In certain embodiments, the acid is hydrochloric acid, hydrobromic acid, acetic acid, trifluoroacetic acid, or succinic acid. In certain embodiments, the acid is methanesulfonic acid. In certain embodiments, the acid is methanesulfonic acid, hydrochloric acid, or hydrobromic acid; and the acid salt of said acyl-amphetamine compound of Formula III is represented by Formula VII:

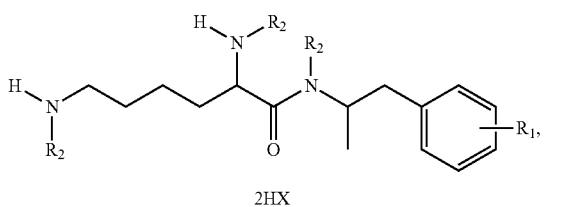

(VII)

2HX wherein:
R$_1$ is hydrogen, halogen, C$_1$-C$_6$ alkyl, or C$_1$-C$_6$ alkoxy;
R$_2$ represents independently for each occurrence hydrogen or C$_1$-C$_6$ alkyl; and
X is —OSO$_2$CH$_3$, Cl, or Br.

In certain embodiments, R$_1$ and R$_2$ are hydrogen. In certain embodiments, the acid is methanesulfonic acid, the acyl-amphetamine compound of Formula III is represented by:

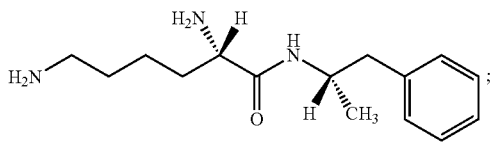 [SMILES: C[C@@H](Cc1ccccc1)NC(=O)[C@@H](N)CCCCN]

and the acid salt of said acyl-amphetamine compound of Formula III is represented by:

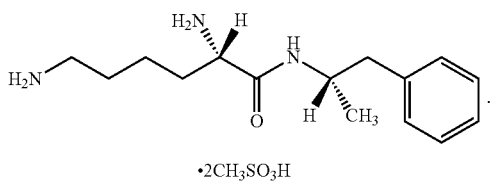

·2CH$_3$SO$_3$H

In certain embodiments, the method comprising admixing a dialkylether solvent (e.g., diethylether, tert-butyl methyl ether, and the like), an acyl-amphetamine compound of Formula III, and an acid to provide an acid salt of said acyl-amphetamine compound of Formula III. One particularly preferred solvent for this reaction comprises a dialkylether, and where the solvent has less than 5% (w/w) or less than 1% (w/w) of alcohol compounds.

In certain embodiments, the method further comprises admixing an acyl-amphetamine compound of Formula III and an acid selected from the group consisting of methanesulfonic acid, hydrochloric acid, or hydrobromic acid to provide an acid salt represented by Formula VIIa:

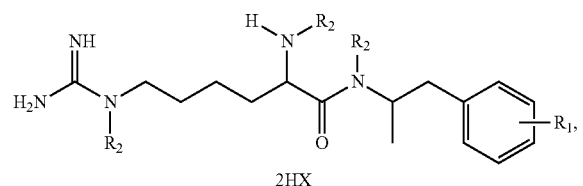

(VIIa)

2HX wherein:
R$_1$ is hydrogen, halogen, C$_1$-C$_6$ alkyl, or C$_1$-C$_6$ alkoxy;
R$_2$ represents independently for each occurrence hydrogen or C$_1$-C$_6$ alkyl; and
X is —OSO$_2$CH$_3$, Cl, or Br.

In certain embodiments, R$_1$ and R$_2$ are hydrogen. In certain embodiments, the acid is hydrochloric acid.

In certain embodiments, the method relates to any one or more of the above methods, wherein the method(s) are carried out on manufacturing scale. In certain embodiments, the method relates to any one or more of the above methods, wherein the method(s) are carried out at a temperature in the range of about −20° C. to about 60° C. In certain embodiments, the method relates to any one or more of the above methods, wherein the method(s) are carried out at a temperature in the range of about 0° C. to about 35° C., or a range of about 10° C. to about 20° C. In certain embodiments, the method relates to any one or more of the above methods, wherein the method(s) are carried out using a solvent system that is amenable to operation in a stainless steel reaction vessel.

In certain embodiments, the method relates to any one or more of the above methods, wherein the method(s) provide the product with a stereoisomeric purity of greater than 90% enantiomeric excess, greater than 95% enantiomeric excess, greater than 98% enantiomeric excess, or greater than 99% enantiomeric excess. In certain embodiments, the method relates to any one or more of the above methods, wherein the method(s) provide the product with a stereoisomeric purity of greater than 90% diastereomeric excess, greater than 95% diastereomeric excess, greater than 98% diastereomeric excess, or greater than 99% diastereomeric excess.

III. Brief Description of Preferred Synthetic Intermediates in the Synthesis of Lisdexamfetamine, Homoarginine-D-Amphetamine and Related Compounds One aspect of the invention provides compounds that are valuable intermediates in the synthesis of amphetamine conjugates. Compounds contemplated to be valuable in the synthesis of amphetamine conjugates are described throughout this disclosure (including the examples) by reference to generic chemical structures and specific compounds, or salts thereof. In certain preferred embodiments, the invention provides a synthetic intermediate compound represented by Formula I, Ia, or II, wherein Formula I is represented by:

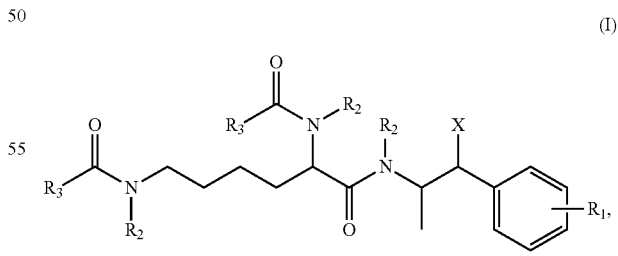

(I)

wherein:
R$_1$ is hydrogen, halogen, C$_1$-C$_6$ alkyl, or C$_1$-C$_6$ alkoxy;
R$_2$ represents independently for each occurrence hydrogen or C$_1$-C$_6$ alkyl;
R$_3$ represents independently for each occurrence C$_1$-C$_6$ alkyl, C$_1$-C$_6$ haloalkyl, C$_1$-C$_6$ alkoxy, or aryl; and
X is Cl, Br, or I; and wherein Formula Ia is represented by:

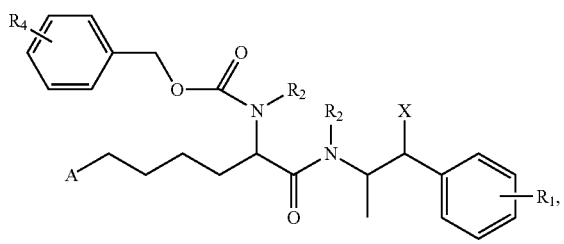

wherein:
A is

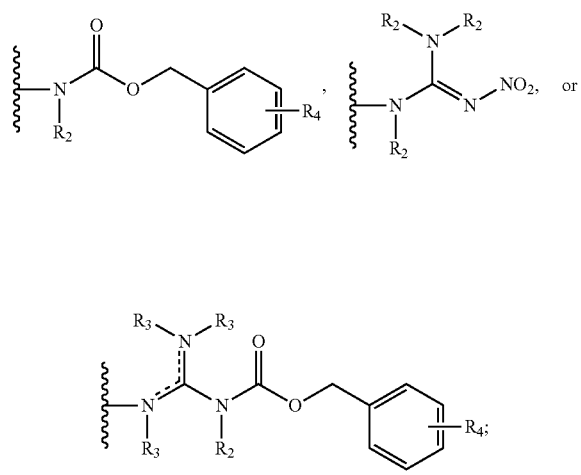

$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl;
$R_3$ is, independently for each occurrence, absent, hydrogen, or

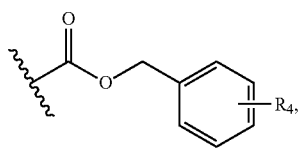

in accordance with the rules of valence and provided that one occurrence of $R_3$ is hydrogen, another occurrence of $R_3$ is absent, and the remaining occurrence of $R_3$ is

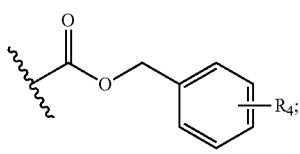

and
$R_4$ represents independently for each occurrence hydrogen, $C_1$-$C_6$ alkyl, halogen, $C_1$-$C_6$ haloalkyl, or $C_1$-$C_6$ alkoxy;

X is Cl, Br, or I; and
wherein Formula II is represented by:

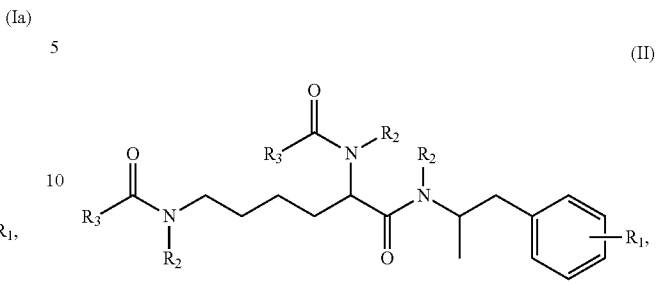

wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl; and
$R_3$ represents independently for each occurrence $C_1$-$C_6$ haloalkyl.

In certain embodiments, the compound is a compound of Formula I. In certain embodiments, $R_1$ is hydrogen. In certain embodiments, $R_2$ is hydrogen. In certain embodiments, $R_3$ is $C_1$-$C_6$ alkyl, $C_1$-$C_6$ haloalkyl, or aryl. In certain embodiments, $R_3$ is $C_1$-$C_6$ haloalkyl, such as trifluoromethyl. In certain embodiments, X is chloro.

In certain embodiments, the compound is a compound of Formula Ia. In certain embodiments, $R_1$ is hydrogen. In certain embodiments, $R_2$ is hydrogen. In certain embodiments, $R_3$ is hydrogen. In certain embodiments, X is chloro.

In certain embodiments, the compound is a compound of Formula II. In certain embodiments, $R_1$ is hydrogen. In certain embodiments, $R_2$ is hydrogen. In certain embodiments, $R_3$ is —$CF_3$.

In certain embodiments, the compound is:

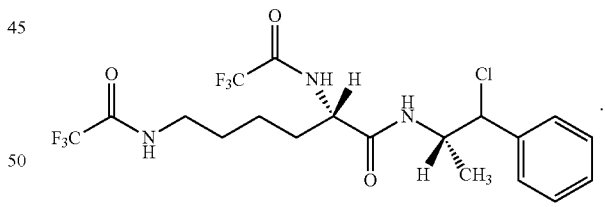

In certain embodiments, the compound is:

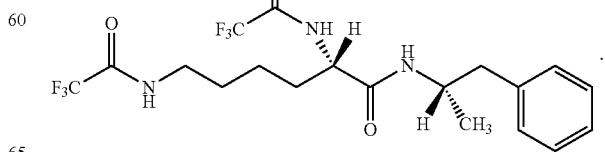

In certain embodiments, the compound is:

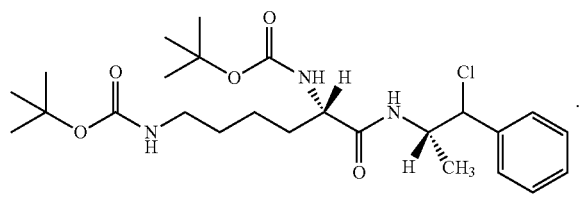 [SMILES: C[C@H](NC(=O)[C@H](CCCCNC(=O)OC(C)(C)C)NC(=O)OC(C)(C)C)C(Cl)c1ccccc1]

In certain embodiments, the compound is:

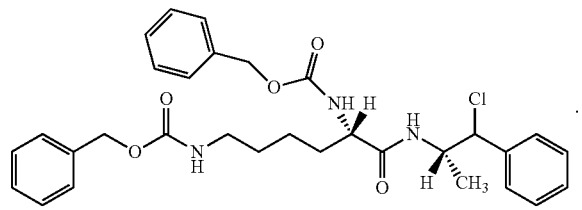 [SMILES: C[C@H](NC(=O)[C@H](CCCCNC(=O)OCc1ccccc1)NC(=O)OCc1ccccc1)C(Cl)c1ccccc1]

In certain embodiments, the compound is:

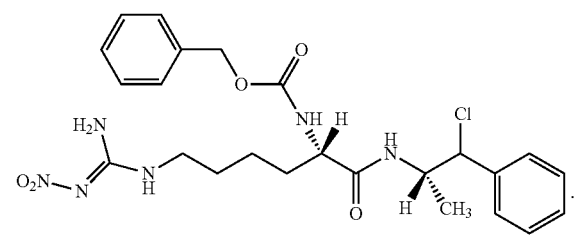 [SMILES: C[C@H](NC(=O)[C@H](CCCCN/C(N)=N/[N+](=O)[O-])NC(=O)OCc1ccccc1)C(Cl)c1ccccc1]

In certain embodiments, the compound is:

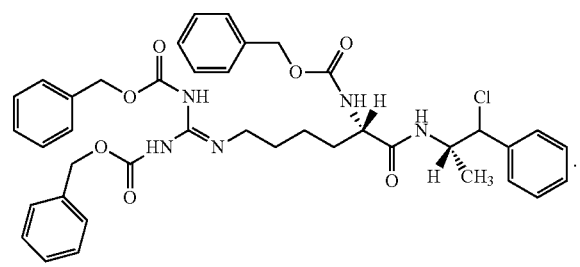 [SMILES: C[C@H](NC(=O)[C@H](CCCCN=C(NC(=O)OCc1ccccc1)NC(=O)OCc1ccccc1)NC(=O)OCc1ccccc1)C(Cl)c1ccccc1]

IV. Compound Salt Forms and Pharmaceutical Compositions

Salts forms of the compounds described herein are contemplated. For example, compounds that contain a basic functional group, such as amino or alkylamino, may be capable of forming a salt when admixed with a suitable acid. Preferably, the salt forms relatively non-toxic, inorganic or organic acid addition salts of compounds described herein. These salts can be prepared by reacting a compound described herein in its free base form with a suitable organic or inorganic acid, and isolating the salt thus formed during subsequent purification. Representative salts include the methanesulfonate, trifluoromethanesulfonate, toluenesulfonic, oxalic, ascorbic, hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, glucoheptonate, lactobionate, and laurylsulphonate salts and the like. (See, for example, Berge et al. (1977) "Pharmaceutical Salts", *J. Pharm. Sci.* 66:1-19)

In other cases, a compound described herein may contain one or more acidic functional groups and, thus, are capable of forming a salt with a base. These salts can be prepared by reacting a compound described herein in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Lisdexamfetamine, homoarginine-D-amphetamine, related compounds, and salts thereof can be formulated in a pharmaceutical composition. Pharmaceutical compositions comprise a therapeutically-effective amount of one or more of the compounds described above, formulated together with one or more pharmaceutically acceptable carriers (additives) and/or diluents. The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

V. Definitions

To facilitate an understanding of the invention, a number of terms and phrases are defined below.

The term "alkyl" is art-recognized and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 10 or fewer carbon atoms in its backbone (e.g., $C_1$-$C_{10}$ for straight chain, $C_3$-$C_{10}$ for branched chain), and alternatively, about 5 or fewer. Likewise, cycloalkyls have from about 3 to about 10 carbon atoms in their ring structure, and alternatively about 5, 6 or 7 carbons in the ring structure. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "aralkyl" refers to an alkyl group substituted with an aryl group.

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "alkoxy" as used herein refers to an alkyl group attached to an oxygen (—O-alkyl). Exemplary alkoxy groups include, but are not limited to, groups with an alkyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, but are not limited to methoxy, ethoxy, propoxy, butoxy, etc.

The term "aryl" is art-recognized and refers to a carbocyclic aromatic group. Representative aryl groups include phenyl, naphthyl, anthracenyl, and the like. The aromatic ring is optionally substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. In certain embodiments, the aromatic ring is not substituted, i.e., an unsubstituted aryl.

The "heteroaryl" is art-recognized and refers to aromatic groups that include at least one ring heteroatom. In certain instances, a heteroaryl group contains 1, 2, 3, or 4 ring heteroatoms. Representative examples of heteroaryl groups includes pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. The heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. The term "haloheteroaryl" refers to an heteroaryl group that is substituted with at least one halogen.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like.

The terms "amine" and "amino" are art-recognized and refer to both unsubstituted and substituted amines, e.g., a moiety that may be represented by the general formulas:

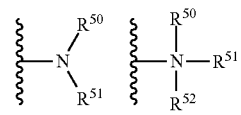

wherein $R^{50}$, $R^{51}$ and $R^{52}$ each independently represent a hydrogen, an alkyl, an alkenyl, —(CH$_2$)$_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—$R^{61}$. Thus, the term "alkylamine" includes an amine group, as defined above, having a substituted or unsubstituted alkyl attached thereto, i.e., at least one of $R^{50}$ and $R^{51}$ is an alkyl group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R$^{61}$, where m and R$^{61}$ are described above.

The symbols "*" and "~~~" used in certain chemical structures indicates the point of attachment of the chemical fragment.

The term "manufacturing scale" refers to a chemical process carried out using at least 30 kg of a reacting agent (e.g., at least 30 kg of L-norephedrine is reacted with the necessary amount of thionyl chloride to provide the Cl-D-Amph-HCl product; See Example 6), or at least about 40 kg, 60 kg, 80 kg, or 100 kg of a reacting agent.

The term "hydrogen source" refers to a composition capable of providing hydrogen during a chemical reduction reaction. Exemplary hydrogen sources include hydrogen gas and ammonium formate.

Certain compounds described herein may exist in particular geometric or stereoisomeric forms. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. For generic chemical structures presented herein, the generic chemical structure is meant to encompass cis- and trans-isomers, a R-enantiomer, a S-enantiomer, diastereomers, and/or mixtures thereof unless the chemical structure or associated definition(s) species otherwise.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

Pharmaceutically acceptable salts of the compounds described herein are contemplated. As used herein, the term "pharmaceutically acceptable salt" refers to any pharmaceutically acceptable salt (e.g., acid or base) of a compound described herein which, upon administration to a subject, is capable of providing a compound of this invention or an active metabolite or residue thereof. As is known to those of skill in the art, "salts" of the compounds described herein may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula NW$_4^+$, wherein W is C$_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecyl sulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the invention compounded with a suitable cation such as Na$^+$, NH$_4^+$, and NW$_4^+$ (wherein W is a C$_{1-4}$ alkyl group), and the like.

As a general matter, compositions specifying a percentage are by weight unless otherwise specified. Further, if a variable is not accompanied by a definition, then the previous definition of the variable controls.

EXAMPLES

The invention now being generally described, will be more readily understood by reference to the following examples, which are included merely for purposes of illustration of certain aspects and embodiments of the invention, and are not intended to limit the invention.

Example I

Preparation of N,N'-Bistrifluoroacetyl-L-Lysine (L-LYS-(TFA)$_2$)

-continued

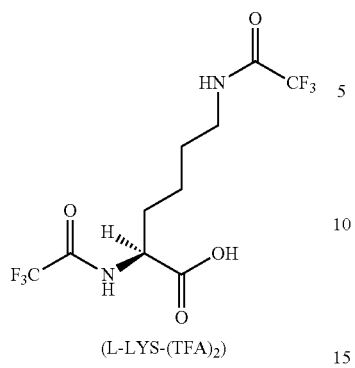

(L-LYS-(TFA)₂)

-continued

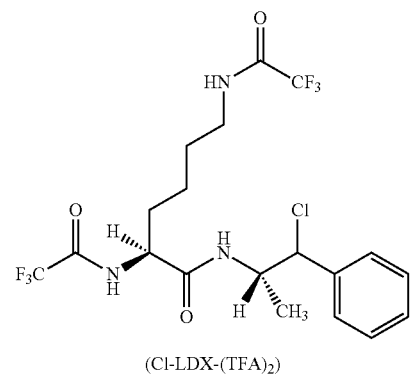

(Cl-LDX-(TFA)₂)

General Experimental Procedure: Assemble a multi-neck 20-liter jacketed reactor fitted with external heating and cooling, mechanical stirring, internal temperature monitor, and nitrogen in/out. Charge 2.0 kg of L-lysine monohydrochloride and 5.3 kg of 32 wt % potassium methoxide in methanol. Dilute the system with an additional 1.5 kg of methanol and heat to about 40° C. After about 30 minutes, charge 3.5 kg of ethyl trifluoroacetate over about 45 minutes. After about 30 minutes at about 40° C., cool the system to about 15° C. Charge 2.9 kg of 4 N hydrochloric acid, and filter all salts. Wash the salt cake with 1.0 kg of methanol, and concentrate the rich filtrate under vacuum at <45° C. to minimum stir volume. Dilute the product mass with 6.0 kg of isopropyl acetate, and wash the new solution with 3.5 kg of 20 wt % aqueous sodium chloride. Concentrate the final solution under vacuum at <45° C. to minimum stir volume. Dilute the product mass with 9.6 kg of isopropyl acetate. This process provided the title compound (~3.7 kg) in approximately quantitative yield as a solution in isopropyl acetate that is used directly in the next synthetic transformation (See Example 2).

Example 2

Preparation of N,N'-Bistrifluoroacetyl-Chloro-Lisdexamfetamine (Cl-LDX-(TFA)₂)

General Experimental Procedure: In Reactor I, assemble a multi-neck 5-liter jacketed reactor fitted with external heating and cooling, mechanical stirring, internal temperature monitor, and nitrogen in/out. To this system is charged a solution of 1.0 kg of N,N'-bistrifluoroacetyl-L-lysine in 2.6 kg of isopropyl acetate (~4 L of solution). The solution is cooled to about −10° C. Then, charge 0.57 kg of Vilsmeier reagent over about 90 minutes, and stir the reaction mixture for another 3-4 hours at about −10° C.

In Reactor II, assemble a multi-neck 20-liter jacketed reactor fitted with external heating and cooling, mechanical stirring, internal temperature monitor, and nitrogen in/out. Charge 1.1 kg of isopropyl acetate, 0.64 kg of chloro-D-amphetamine hydrochloride (Cl-D-Amph-HCl), and 6.0 kg of 20% aqueous potassium bicarbonate. Cool the reaction system to about 5° C. With vigorous agitation, charge the contents of Reaction I into Reactor II, rinsing Reaction I with 0.84 kg of isopropyl acetate. After about 30 minutes, warm the contents of Reactor 2 to about 20° C., stop the stirring, and remove the lower aqueous phase. The resultant slurry contains the title compound (~95 mol % crude yield, 1.4 kg) and can be used directly in the next step.

Example 3

Preparation of N,N'-Bistrifluoroacetyl-Lisdexamfetamine (LDX-(TFA)₂)

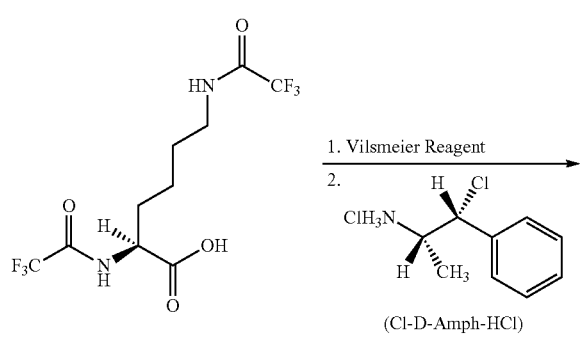

(Cl-D-Amph-HCl)

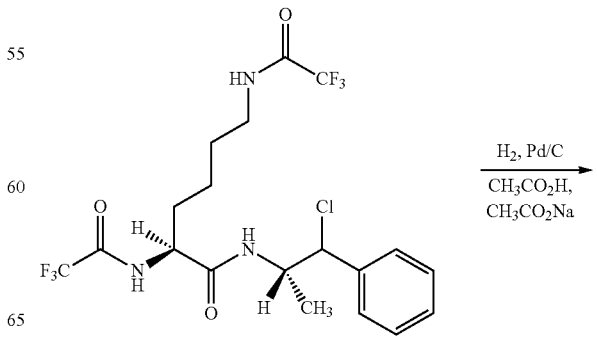

-continued

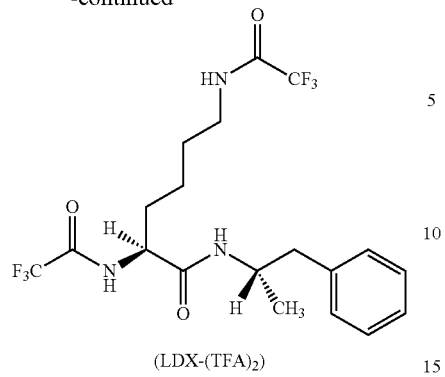

(LDX-(TFA)₂)

General Experimental Procedure: Assemble a multi-neck 20-liter jacketed reactor fitted with external heating and cooling, mechanical stirring, internal temperature monitor, vacuum port, and gas in/out. Concentrate the slurry from the previous step (i.e., solution product from Example 2) under vacuum at <45° C. to minimum stir volume. Charge 12.9 kg of acetic acid and warm to about 50° C. Charge 0.28 kg of sodium acetate and 14 g of 10 wt % Pd/C (50% wet). Purge the system six times by alternate evacuation/nitrogen charge. Charge the system six times by alternate evacuation/hydrogen charge, leaving the system under slight hydrogen pressure (balloon). Stir until reaction completion by HPLC (5 hours). Purge the system six times by alternate evacuation/ nitrogen charge. Cool to about 10° C. and charge 8.4 kg of water. Filter the slurry, wash with 4.2 kg of water, and discard the filtrate. Suspend the filter cake in 9.8 kg of acetone at 30 to 40° C. Filter the catalyst and transfer the rich filtrate to a clean 20-liter jacketed reactor fitted with external heating and cooling, mechanical stirring, internal temperature monitor, and nitrogen in/out. Concentrate the solution under vacuum at <40° C. to final volume (~8 L). Charge 8.4 kg of water and cool the new slurry to about 10° C. Filter the product, wash the filter cake with water (4.2 kg), and dry the filter cake to provide the title compound as a free-flowing powder (~1.5 kg, ~25% wet). The wet material may be used directly in the next synthetic step, or the wet material may be dried under vacuum at about 50° C. to give the title compound as a dried solid (~1 kg, 85 mol %).

Example 4

Preparation of Lisdexamfetamine (LDX)

-continued

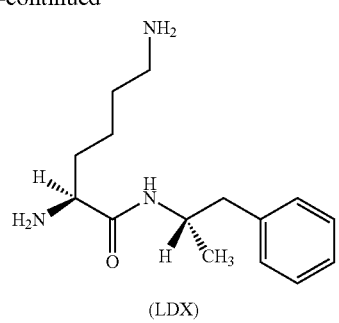

(LDX)

General Experimental Procedure: Assemble a multi-neck 6-liter jacketed reactor fitted with bottom valve, external heating and cooling, mechanical stirring, internal temperature monitor, and gas in/out. Charge 501 g of LDX-(TFA)₂ (28% water-wet material from the previous step, i.e., Example 3), 760 g of water, and 452 g of 50% aqueous sodium hydroxide. Agitate at ~45° C. until complete by HPLC analysis. Cool to ~20° C. and charge 275 g of 2-methyl tetrahydrofuran. Stop the agitation and remove the aqueous phase. Charge 330 g of water, and 226 g of 50% aqueous sodium hydroxide. Agitate at ~20° C. Stop the agitation and remove the aqueous phase. Charge 540 g of 2-methyl tetrahydrofuran and 162 g of sodium hydroxide. Agitate at ~20° C. Stop the agitation and remove the aqueous phase. Charge 1075 g of 2-methyl tetrahydrofuran and 162 g of sodium hydroxide, and 162 g of Celatom. Filter the slurry, and rinse the filter cake with 1892 g of 2-methyl tetrahydrofuran to provide the title compound as a solution in 2-methyl tetrahydrofuran. This solution can be used directly in the next step.

Example 5

Preparation of Lisdexamfetamine Dimesylate

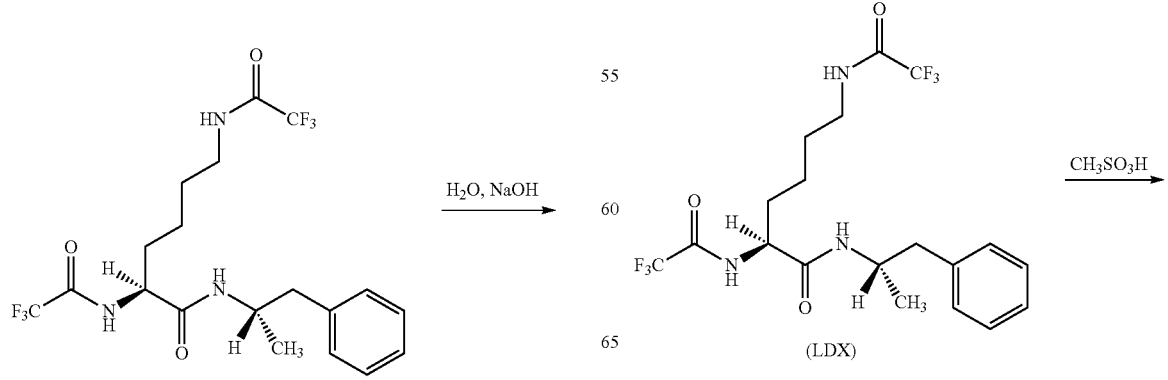

(LDX)

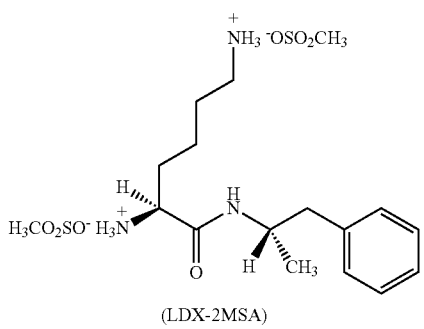

(LDX-2MSA)

General Experimental Procedure: Warm the LDX-containing solution from Example 4 to ~45° C. and charge 156 g of methanesulfonic acid over ~1 hour. Charge 1150 g of tert butyl methyl ether. Cool the new slurry to about 15° C. Filter the solution, wash the filter cake with 2350 g of tert butyl methyl ether, and dry the filter cake on the filter to provide the title compound as a free-flowing powder. Then, further dry the powder under vacuum at about 45° C. to provide the title compound (345 g, approximately 95 mol % yield) as a white solid.

Example 6

Preparation of Chloro-D-Amphetamine Hydrochloride (Cl-D-Amph-HCl)

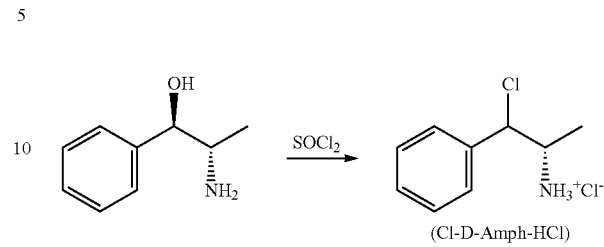

General Experimental Procedure: L-norephedrine (200 g) and toluene (2075 g) are charged to a reaction flask. The solution is stirred while slowly adding a charge of 197.4 g of thionyl chloride. The reaction mixture so-formed is stirred at 55-60° C. for 3-6 hours. The reaction conversion is determined by HPLC. The reaction mixture is cooled to less than 10° C. with stirring and chlorodextroamphetamine hydrochloride precipitates. The precipitated solids are isolated by filtration and washed twice with 865 g of toluene. The product wet cake is dried in a vacuum oven to yield 252 g (92%) of the title compound.

Example 7

Preparation of N,N'-Biscarbobenzyloxy-Chloro-Lisdexamfetamine (Cl-D-LDX-(Cbz)$_2$)

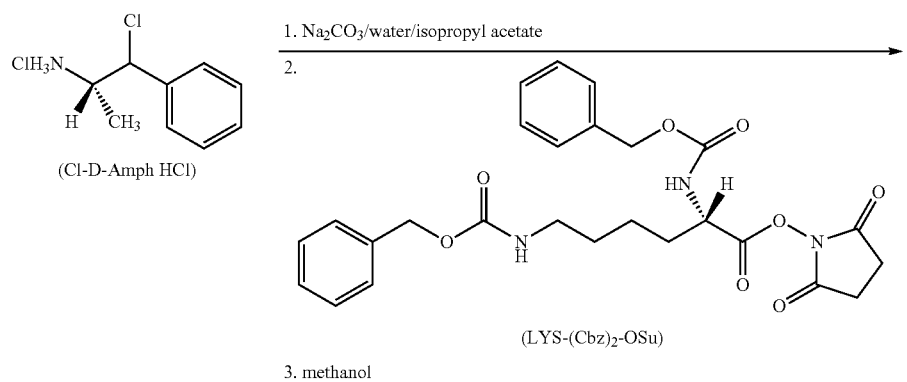

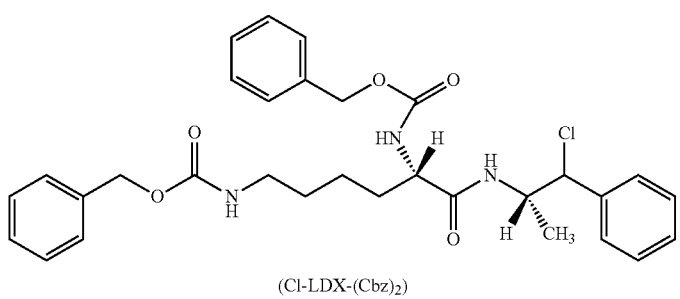

General Experimental Procedure: In an appropriately sized, inert jacketed reactor charge 50.0 g of Cl-D-Amph HCl. Charge 125.0 g of water and agitate until the solids dissolve. Add 654.0 g of isopropyl acetate. Charge 23.1 g of sodium carbonate keeping the batch temperature 20-25° C. and stir ~30 minutes. Wash the organic phase with a solution of 49.8 g sodium chloride in 150.0 g of water. Remove the aqueous phase. With vigorous agitation charge 131.5 g of Cl-LYS-(Cbz)$_2$-OSu in portions to the batch keeping the temperature less than 30° C. Heat the batch to ~50° C. until the reaction is complete by HPLC analysis. Cool the batch to ~5° C. and filter the slurry. Rinse the wet cake with 87.2 g of cold isopropyl acetate, and dry on the filter under nitrogen. To a clean, dry reactor charge the crude solids followed by 858 g of methanol. Heat the slurry to ~65° C. for 2 hours. Cool the batch to ~5° C. and filter the slurry. Rinse the wet cake with 301 g of cold methanol, and vacuum dry ~55° C. to give the product as an off-white solid (107.0 g, 78 mol %).

Example 8

Alternative Preparation of N,N'-Biscarbobenzyloxy-Chloro-Lisdexamfetamine (Cl-D-LDX-(Cbz)$_2$)

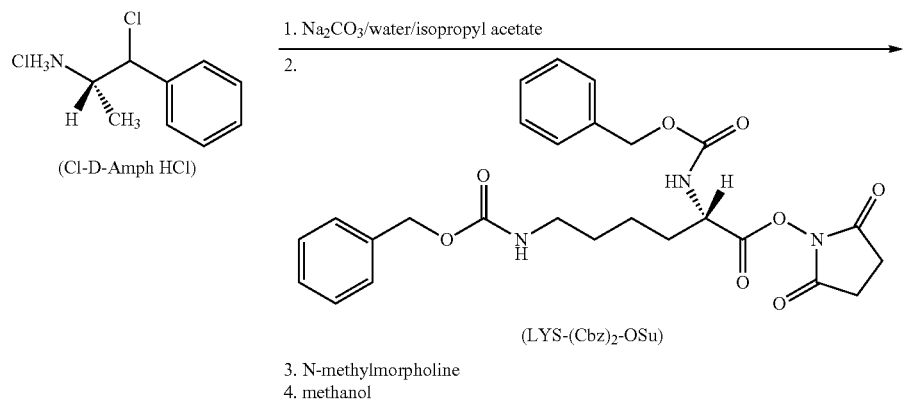

1. Na$_2$CO$_3$/water/isopropyl acetate
2.
3. N-methylmorpholine
4. methanol

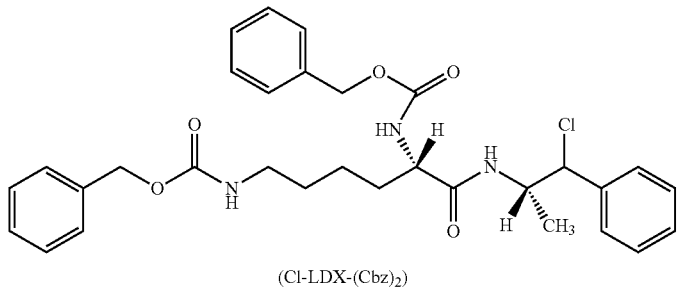

(Cl-LDX-(Cbz)$_2$)

General Experimental Procedure: In an appropriately sized, inert jacketed reactor charge 50.0 g of Cl-D-Amph HCl. Charge 125.0 g of water and agitate until the solids dissolve. Add 654.0 g of isopropyl acetate. Charge 23.1 g of sodium carbonate keeping the batch temperature 20-25° C. and stir ~30 minutes. Wash the organic phase with a solution of 49.8 g sodium chloride in 150.0 g of water. Remove the aqueous phase. With vigorous agitation charge 131.5 g of Cl-LYS-(Cbz)$_2$-OSu in portions to the batch keeping the temperature less than 30° C. Charge 27.4 g of N-methylmorpholine to the batch keeping the temperature less than 30° C. Heat the batch to ~50° C. until the reaction is complete by HPLC analysis. Cool the batch to ~5° C. and filter the slurry. Rinse the wet cake with 87.2 g of cold isopropyl acetate, and dry on the filter under nitrogen. To a clean, dry reactor charge the crude solids followed by 858 g of methanol. Heat the slurry to ~65° C. for 2 hours. Cool the batch to ~5° C. and filter the slurry. Rinse the wet cake with 301 g of cold methanol, and vacuum dry ~55° C. to give the product as an off-white solid (107.0 g, 78 mol %).

Example 9

Preparation of Lisdexamfetamine Dimesylate

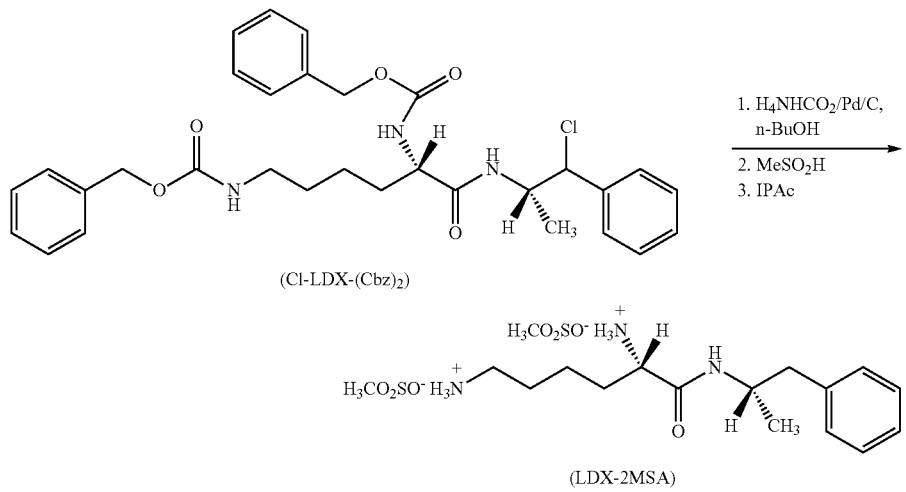

General Experimental Procedure: In an appropriately sized, inert jacketed reactor charge 50.0 g of Cl-D-LDX-(Cbz)$_2$, 3.25 g of 10% (50% wet) palladium on carbon and 303.8 g of n-butanol. To the stirred batch, add 27.8 g of ammonium formate. Heat the batch at 55-65° C. until the reaction is complete by HPLC. Hot filter the batch. Charge 17.8 g of methanesulfonic acid keeping the batch temperature 45-65° C. Stir the resulting batch at 55-65° C. for 2 hours after crystallization is observed. Charge between 163.5 g and 327 g of isopropyl acetate (IPAc) over ~1.5 hours and stir at a temperature of 55-65° C. for 2 hours. Cool the batch to ~20° C. over 3 hours and hold for 4 hours. Cool the batch to 3° C. and hold for 12-16 hours. Filter the slurry and wash the wet cake with 43.6 g of chilled isopropyl acetate. Vacuum dry at ~50° C. to give the product as a white solid (35.8 g, 89 mol %).

Example 10

Alternative Preparation of Lisdexamfetamine Dimesylate

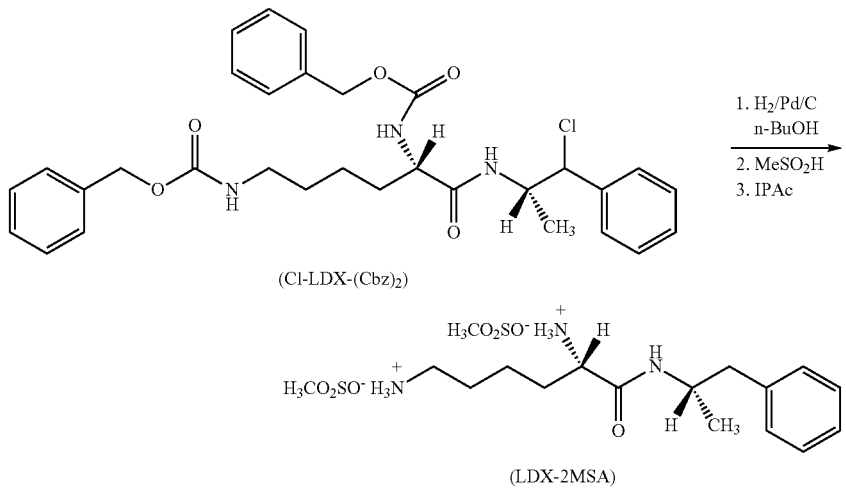

General Experimental Procedure: In an appropriately sized, inert jacketed reactor charge 50.0 g of Cl-D-LDX-(Cbz)$_2$, 3.25 g of 10% (50% wet) palladium on carbon and 303.8 g of n-butanol. Purge the system six times by alternate evacuation/nitrogen charge. Charge the system six times by alternate evacuation/hydrogen charge, leaving the system under ~150 psi hydrogen. Heat the batch to ~80° C. until the reaction is complete by HPLC. Purge the system six times by alternate evacuation/nitrogen charge. Hot filter the batch. Charge 17.8 g of methanesulfonic acid keeping the batch temperature 45-65° C. Stir the resulting batch at 55-65° C. for 2 hours after crystallization is observed. Charge between 163.5 g and 327 g of isopropyl acetate (IPAc) over ~1.5 hours and stir 55-65° C. for 2 hours. Cool the batch to ~20° C. over 3 hours and hold for 4 hours. Cool the batch to 3° C. and hold for 12-16 hours. Filter the slurry and wash the wet cake with 43.6 g of chilled isopropyl acetate. Vacuum dry at ~50° C. to give the product as a white solid (24.7 g, 68 mol %).

Incorporation By Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of preparing an acyl-amphetamine compound of Formula III, comprising:
    (a) admixing an acyl-halamphetamine compound of Formula I, a hydrogenation catalyst, and hydrogen gas to provide an acyl-amphetamine compound of Formula II; which acyl-amphetamine compound of Formula II is admixed with a deprotecting agent to provide an acyl-amphetamine compound of Formula III; or
    (b) admixing an acyl-halamphetamine compound of Formula I and a deprotecting agent to provide an acyl-halamphetamine compound of Formula IIa; which acyl-halamphetamine compound of Formula IIa is admixed with a hydrogenation catalyst and hydrogen gas to provide an acyl-amphetamine compound of Formula III;
    wherein the acyl-halamphetamine compound of Formula I is represented by:

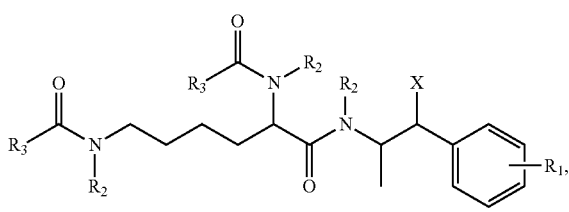

(I)

wherein:
    $R_1$ is hydrogen, halogen, $C_1$-$C_6$ alkyl, or $C_1$-$C_6$ alkoxy;
    $R_2$ represents independently for each occurrence hydrogen or $C_1$-$C_6$ alkyl;
    $R_3$ represents independently for each occurrence $C_1$-$C_6$ alkyl, $C_1$-$C_6$ haloalkyl, $C_1$-$C_6$ alkoxy, or aryl; and
    X is Cl, Br, or I;
wherein the acyl-amphetamine compound of Formula II is represented by:

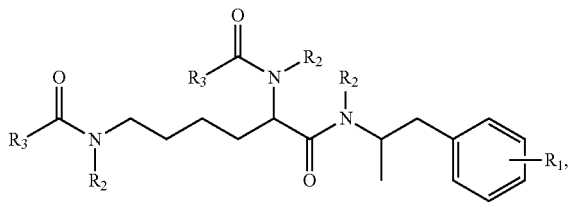

(II)

wherein:
    $R_1$ is hydrogen, halogen, $C_1$-$C_6$ alkyl, or $C_1$-$C_6$ alkoxy;
    $R_2$ represents independently for each occurrence hydrogen or $C_1$-$C_6$ alkyl; and
    $R_3$ represents independently for each occurrence $C_1$-$C_6$ alkyl, $C_1$-$C_6$ haloalkyl, $C_1$-$C_6$ alkoxy, or aryl;
wherein the acyl-halamphetamine compound of Formula IIa is represented by:

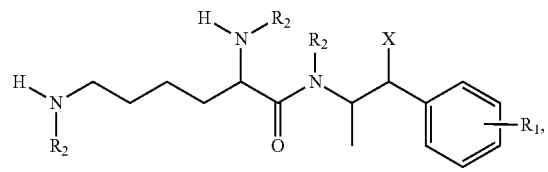

(IIa)

wherein:
    $R_1$ is hydrogen, halogen, $C_1$-$C_6$ alkyl, or $C_1$-$C_6$ alkoxy;
    $R_2$ represents independently for each occurrence hydrogen or $C_1$-$C_6$ alkyl; and
    X is Cl, Br, or I; and
the acyl-amphetamine compound of Formula III is represented by:

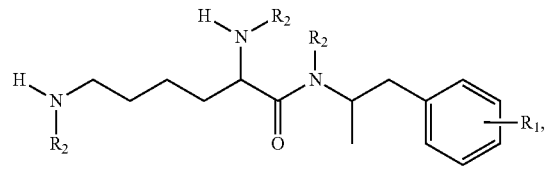

(III)

wherein:
    $R_1$ is hydrogen, halogen, $C_1$-$C_6$ alkyl, or $C_1$-$C_6$ alkoxy; and
    $R_2$ represents independently for each occurrence hydrogen or $C_1$-$C_6$ alkyl.

2. The method of claim 1, wherein $R_1$ is hydrogen.
3. The method of claim 1, wherein $R_2$ is hydrogen.
4. The method of claim 3, wherein $R_3$ is $C_1$-$C_6$ haloalkyl.
5. The method of claim 3, wherein $R_3$ is trifluoromethyl.
6. The method of claim 1, wherein the hydrogenation catalyst comprises palladium.
7. The method of claim 1, wherein the hydrogenation catalyst comprises palladium on carbon.
8. The method of claim 7, wherein the step requiring admixing a hydrogenation catalyst and hydrogen gas further comprises admixing acetic acid.
9. The method of claim 8, further comprising isolating the acyl-amphetamine compound of Formula II as a solid comprising from about 15% (w/w) to about 40% (w/w) water.

10. The method of claim 8, further comprising crystallizing the acyl-amphetamine compound of Formula II from a mixture comprising acetic acid and water.

11. The method of claim 1, wherein after the acyl-amphetamine compound of Formula II is admixed with a deprotecting agent to provide an acyl-amphetamine compound of Formula III, the method further comprises admixing an alkyl tetrahydrofuran and isolating the acyl-amphetamine compound of Formula III.

12. The method of claim 1, wherein the deprotecting agent comprises a base and a compound R$_4$—OH, wherein R$_4$ is hydrogen, C$_1$-C$_6$ alkyl, or aryl.

13. The method of claim 12, wherein the base is an alkali metal hydroxide.

14. The method of claim 1, wherein the deprotecting agent is a mixture of sodium hydroxide and water.

15. The method of claim 1, wherein the method comprises admixing an acyl-halamphetamine compound of Formula I, a hydrogenation catalyst, and hydrogen gas to provide an acyl-amphetamine compound of Formula II; which acyl-amphetamine compound of Formula II is admixed with a deprotecting agent to provide an acyl-amphetamine compound of Formula III.

16. The method of claim 1, wherein the acyl-halamphetamine compound of Formula I is represented by:

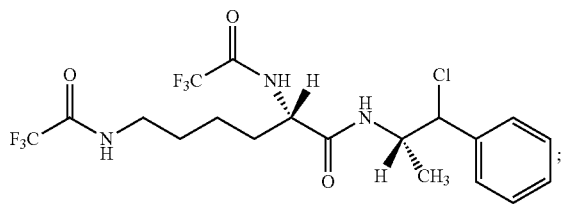 [SMILES: C[C@H](NC(=O)[C@H](CCCCNC(=O)C(F)(F)F)NC(=O)C(F)(F)F)C(Cl)c1ccccc1]

the acyl-amphetamine compound of Formula II is represented by:

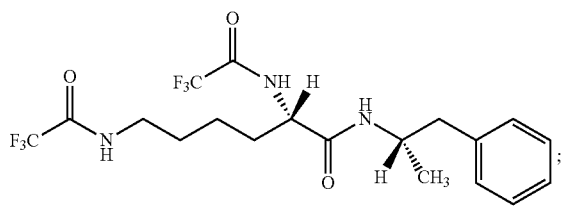 [SMILES: C[C@@H](Cc1ccccc1)NC(=O)[C@H](CCCCNC(=O)C(F)(F)F)NC(=O)C(F)(F)F]

and
the acyl-amphetamine compound of Formula III is represented by:

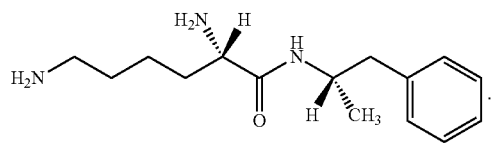 [SMILES: C[C@@H](Cc1ccccc1)NC(=O)[C@@H](N)CCCCN]

17. A method of preparing an acyl-amphetamine compound, comprising admixing an acyl-halamphetamine compound of Formula Ia, a hydrogenation catalyst, and a hydrogen source to provide an acyl-amphetamine compound of Formula III, wherein the acyl-halamphetamine compound of Formula Ia is represented by:

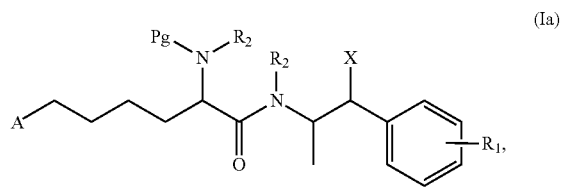

wherein:

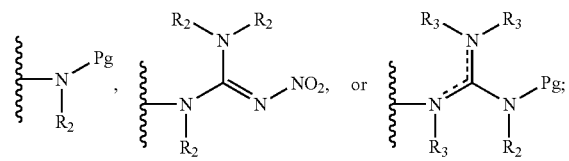

A is

Pg is a protecting group that undergoes deprotection under hydrogenation conditions;

R$_1$ is hydrogen, halogen, C$_1$-C$_6$ alkyl, or C$_1$-C$_6$ alkoxy;

R$_2$ represents independently for each occurrence hydrogen or C$_1$-C$_6$ alkyl;

R$_3$ is, independently for each occurrence, absent, hydrogen, or Pg, in accordance with the rules of valence and provided that one occurrence of R$_3$ is hydrogen, another occurrence of R$_3$ is absent, and the remaining occurrence of R$_3$ is Pg; and X is Cl, Br, or I; and wherein the acyl-amphetamine compound of Formula III is represented by:

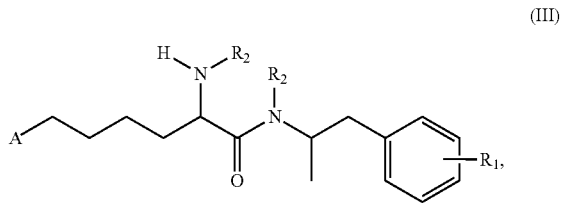

wherein:

R$_1$ is hydrogen, halogen, C$_1$-C$_6$ alkyl, or C$_1$-C$_6$ alkoxy;

R$_2$ represents independently for each occurrence hydrogen or C$_1$-C$_6$ alkyl;

A is —N(H)R$_2$ or

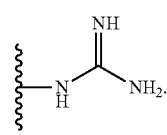

18. The method of claim 1, further comprising admixing a halamphetamine compound of Formula IV and a protected lysine compound of Formula V to provide a compound of Formula I; wherein the halamphetamine compound of Formula IV is represented by:

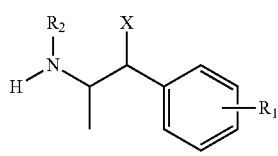

or a salt thereof, wherein:

$R_1$ is hydrogen, halogen, $C_1$-$C_6$ alkyl, or $C_1$-$C_6$ alkoxy;

$R_2$ represents independently for each occurrence hydrogen or $C_1$-$C_6$ alkyl; and X is Cl, Br, or I; and wherein the protected lysine compound of Formula V is represented by:

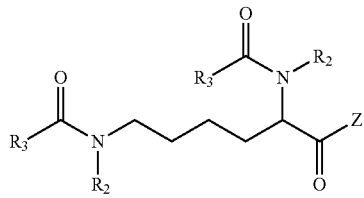

wherein:

$R_2$ represents independently for each occurrence hydrogen or $C_1$-$C_6$ alkyl; and $R_3$ represents independently for each occurrence $C_1$-$C_6$ alkyl, $C_1$-$C_6$ haloalkyl, $C_1$-$C_6$ alkoxy, or aryl; and Z is a leaving group.

19. The method of claim 18, wherein the compound of Formula I is represented by:

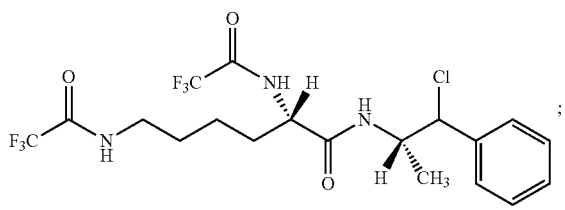 [SMILES: C[C@H](NC(=O)[C@H](CCCCNC(=O)C(F)(F)F)NC(=O)C(F)(F)F)C(Cl)c1ccccc1]

the acyl-amphetamine compound of Formula II is represented by:

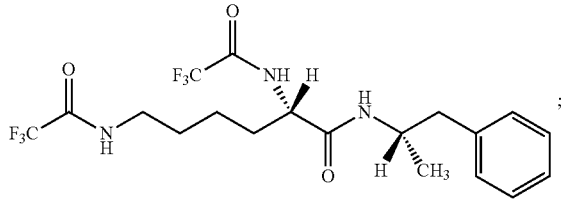 [SMILES: C[C@@H](Cc1ccccc1)NC(=O)[C@H](CCCCNC(=O)C(F)(F)F)NC(=O)C(F)(F)F]

the acyl-halamphetamine compound of Formula IIa is represented by:

the acyl-amphetamine compound of Formula III is represented by:

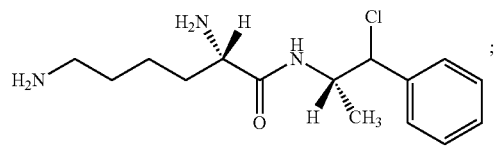 [SMILES: C[C@H](NC(=O)[C@@H](N)CCCCN)C(Cl)c1ccccc1]

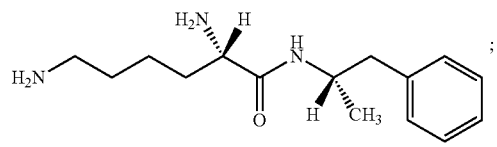 [SMILES: C[C@@H](Cc1ccccc1)NC(=O)[C@@H](N)CCCCN]

the halamphetamine compound of Formula IV is represented by:

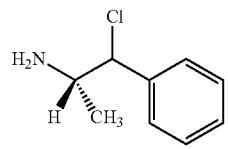

or a hydrochloride salt thereof; and the protected lysine compound of Formula V is represented by:

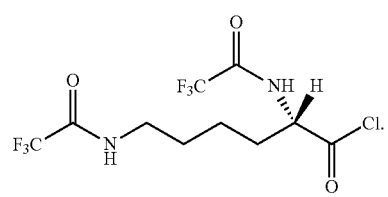 [SMILES: O=C(Cl)[C@H](CCCCNC(=O)C(F)(F)F)NC(=O)C(F)(F)F]

20. The method of claim 18, wherein Z is chloro, bromo, fluoro, iodo, or

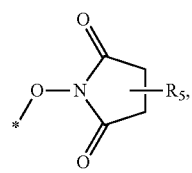

wherein $R_5$ is hydrogen or $C_1$-$C_6$ alkyl.

21. The method of claim 18, further comprising admixing water and alkali metal bicarbonate.

22. The method of claim 18, further comprising admixing a norephedrine compound of Formula VI and a halogenating agent to provide a halamphetamine compound of Formula IV; wherein the norephedrine compound of Formula VI is represented by:

(VI)

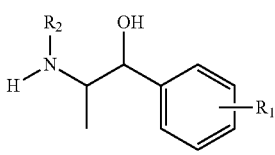

or a salt thereof, wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl.

23. The method of claim 1, further comprising admixing an acyl-amphetamine compound of Formula III and an acid to provide an acid salt of said acyl-amphetamine compound of Formula III.

24. A compound of Formula I, Ia, or II, wherein Formula I is represented by:

(I)

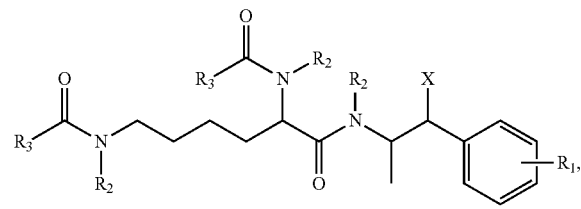

wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl;
$R_3$ represents independently for each occurrence $C_1$-$C_6$ alkyl, $C_1$-$C_6$ haloalkyl, $C_1$-$C_6$ alkoxy, or aryl; and
X is Cl, Br, or I;
wherein Formula Ia is represented by:

(Ia)

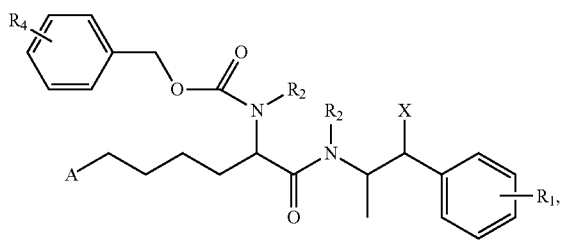

wherein:

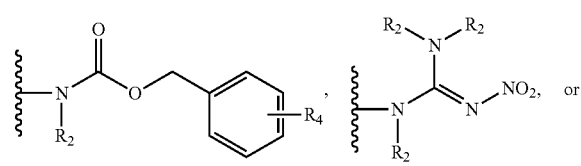

-continued

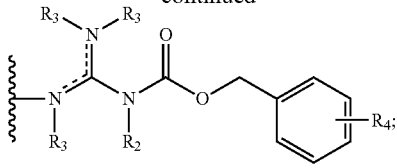

A is
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl;
$R_3$ is, independently for each occurrence, absent, hydrogen, or

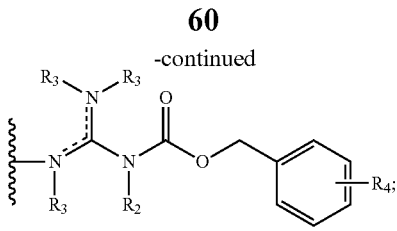

in accordance with the rules of valence and provided that one occurrence of $R_3$ is hydrogen, another occurrence of $R_3$ is absent, and the remaining occurrence of $R_3$ is

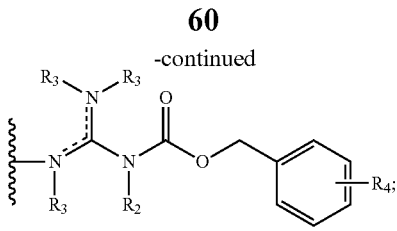

and
$R_4$ represents independently for each occurrence hydrogen, $C_1$-$C_6$ alkyl, halogen, $C_1$-$C_6$ haloalkyl, or $C_1$-$C_6$ alkoxy;
X is Cl, Br, or I; and
wherein Formula II is represented by:

(II)

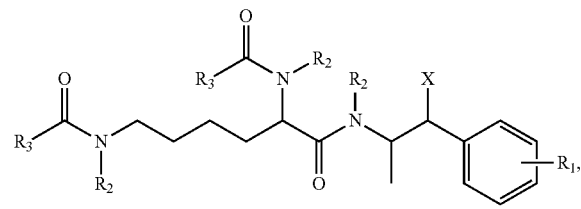

wherein:
$R_1$ is hydrogen, halogen, $C_1$-$C_6$ alkyl, or $C_1$-$C_6$ alkoxy;
$R_2$ represents independently for each occurrence hydrogen or $C_1$-$C_6$ alkyl; and
$R_3$ represents independently for each occurrence $C_1$-$C_6$ haloalkyl.

* * * * *

UNITED STATES PATENT AND TRADEMARK OFFICE
CERTIFICATE OF CORRECTION

PATENT NO. : 8,614,346 B2  
APPLICATION NO. : 13/378176  
DATED : December 24, 2013  
INVENTOR(S) : Jass et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this  
Twenty-second Day of September, 2015

Michelle K. Lee  
*Director of the United States Patent and Trademark Office*